(12) United States Patent
Okamura

(10) Patent No.: US 7,367,226 B2
(45) Date of Patent: May 6, 2008

(54) INTERFACE DETECTION APPARATUS AND METHOD FOR DETECTING HIDDEN INTERFACE USING MICROWAVE

(75) Inventor: Seichi Okamura, Hamamatsu (JP)

(73) Assignee: President of Shizuoka University, Shizuoka-shi (JP)

( * ) Notice: Subject to any disclaimer, the term of this patent is extended or adjusted under 35 U.S.C. 154(b) by 423 days.

(21) Appl. No.: 10/812,879

(22) Filed: Mar. 31, 2004

(65) Prior Publication Data

US 2005/0156607 A1    Jul. 21, 2005

(30) Foreign Application Priority Data

Jan. 19, 2004    (JP)    ............... 2004-011147

(51) Int. Cl.
*G01F 23/284*    (2006.01)
*G01R 27/04*    (2006.01)
(52) U.S. Cl. ............... 73/64.55; 324/639; 250/357.1
(58) Field of Classification Search ............... 73/64.55; 324/639; 250/346, 357.1
See application file for complete search history.

(56) References Cited

U.S. PATENT DOCUMENTS 2,982,170 A * 5/1961 Wyss ............... 73/64.55
3,499,154 A * 3/1970 Boyd ............... 250/338.1
6,853,199 B2 * 2/2005 Noik et al. ............... 324/637
2003/0141456 A1 * 7/2003 Mc Neal et al. ............... 250/357.1

FOREIGN PATENT DOCUMENTS

JP    2001-83102    3/2001

* cited by examiner

*Primary Examiner*—Daniel S Larkin
(74) *Attorney, Agent, or Firm*—Oblon, Spivak, McClelland, Maier & Neustadt, P.C.

(57)    ABSTRACT

An interface detection apparatus detects a position of a hidden interface between first and second materials, the first material having a different physical property from the second material. The apparatus encompasses (a) an irradiation mechanism configured to irradiate an electromagnetic wave onto a sample implemented by the first and second materials, (b) a detection mechanism configured to detect the electromagnetic wave that has passed through the sample, and (c) a traveling mechanism configured to change the relative position of the hidden interface with respect to the position of the detection mechanism.

16 Claims, 11 Drawing Sheets

US 7,367,226 B2

INTERFACE DETECTION APPARATUS AND METHOD FOR DETECTING HIDDEN INTERFACE USING MICROWAVE

BACKGROUND OF THE INVENTION

1. Field of the Invention

The present invention relates to a measurement technology using electromagnetic waves. The invention particularly relates to an interface detection apparatus and method for detecting the hidden interface of materials employing the near-field region (the Fresnel region) antenna technology.

2. Description of the Related Art

There is a case where a hidden interface such as an interface between air and liquid contained in an opaque glass or an opaque plastic container must be detected externally. Since there is no earlier method of detecting the internal liquid level if, in particular, a container is opaque or has an opaque sheet such as paper attached on the surface, the position thereof has to be found through visual observation from the inlet disposed above, and necessary operations for detecting precisely the hidden liquid level must then be carried out. A hidden interface detection apparatus, which detects the hidden interface of materials externally from an opaque container without making contact with inner hidden materials contained in them, has been in demand in order to automate those operations. However, at present, no appropriate hidden interface detection apparatus and method has been known.

SUMMARY OF THE INVENTION

In view of these situations, it is an object of the present invention to provide an interface detection apparatus and method capable of detecting the hidden interface of materials in an optically opaque environment externally without making contact with the same.

An aspect of the present invention inheres in an interface detection apparatus for detecting a position of a hidden interface between first and second materials, the first material having a different physical property from the second material, encompassing (a) an irradiation mechanism configured to irradiate an electromagnetic wave onto a sample implemented by the first and second materials; (b) a detection mechanism configured to detect the electromagnetic wave that has passed through the sample; and (c) a traveling mechanism configured to change the relative position of the hidden interface with respect to the position of the detection mechanism.

Another aspect of the present invention inheres in an interface detection method for detecting the position of a hidden interface between first and second materials, the first material having a different physical property from the second material, encompassing:

(a) irradiating an electromagnetic wave onto a sample implemented by the first and second materials;

(b) detecting the electromagnetic wave that has passed through the sample by a detection mechanism;

(c) changing relative positions of the hidden interface with respect to the position of the detection mechanism; and (d) determining an absolute position of the hidden interface with respect to a reference position.

Still another aspect of the present invention inheres in an interface detection apparatus for detecting the position of a hidden interface between first and second materials, the first material having a different physical property from the second material, encompassing (a) means for irradiating an electromagnetic wave onto a sample implemented by the first and second materials; (b) means for detecting the electromagnetic wave that has passed through the sample; and (c) means for changing the relative position of the hidden interface with respect to the position of the detection mechanism.

Other and further objects and features of the present invention will become obvious upon an understanding of the illustrative embodiments about to be described in connection with the accompanying drawings or will be indicated in the appended claims, and various advantages not referred to herein will occur to one skilled in the art upon employing of the present invention in practice.

BRIEF DESCRIPTION OF THE DRAWINGS

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

Generally and as it is conventional in the representation of detection apparatuses, it will be appreciated that the various drawings are not drawn to scale from one figure to another nor inside a given figure, and in particular that the layer thicknesses are arbitrarily drawn for facilitating the reading of the drawings.

DETAILED DESCRIPTION OF THE EMBODIMENTS

In the following description, specific details are set forth, such as specific materials, process and equipment in order to provide a thorough understanding of the present invention. It will be apparent, however, to one skilled in the art that the present invention may be practiced without these specific details. In other instances, well-known manufacturing materials, process and equipment are not set forth in detail in order not to unnecessary obscure the present invention.

First Embodiment

Figure 1A:
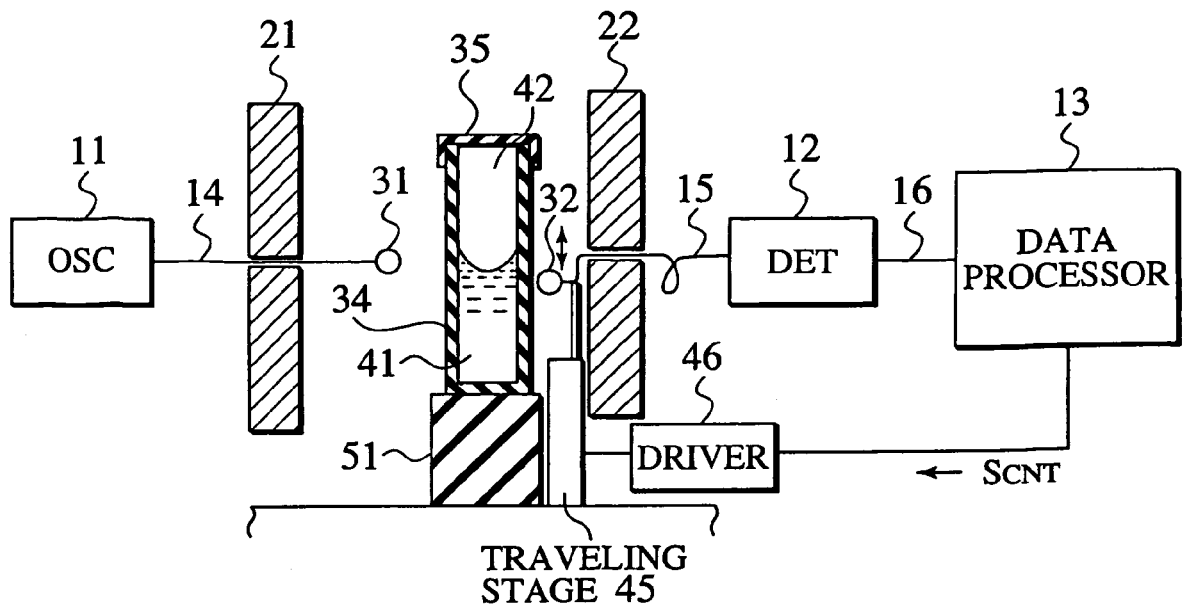
FIG. 1A is a schematic diagram for describing the configuration of an interface detection apparatus according to a first embodiment of the present invention.

As shown in FIG. 1A, an interface detection apparatus according to a first embodiment of the present invention encompasses an irradiation mechanism (11, 14, 31), which irradiates electromagnetic waves onto a sample (34, 35, 41, 42) having a hidden interface formed between layered materials with different physical properties, a detection mechanism (32, 15, 12), which detects electromagnetic waves that have passed through the sample (34, 35, 41, 42), and a traveling mechanism (45, 46), which changes the relative position of the hidden interface of the materials with respect to the detection mechanism (32, 15, 12). The sample (34, 35, 41, 42) includes a first material 41 and a second material 42 contained in container 34. The container 34 has a lid 35 that seals this container 34. Generally, the lid 35 does not have to completely seal the container 34. Anyhow, the lid 35 may be omitted according to circumstances or measurement specifications.

In the interface detection apparatus according to the first embodiment, the irradiation mechanism (11, 14, 31) includes an oscillator (OSC) 11 configured to generate the electromagnetic wave, a transmitter side cable 14, which is connected to the oscillator 11, and a radiation antenna (transmitting antenna) 31, which is connected to the transmitter side cable 14 so that the radiation antenna 31 can be electrically connected to the oscillator 11. The radiation antenna 31 radiates the electromagnetic wave onto the sample (34, 35, 41, 42).

In addition, the detection mechanism (32, 15, 12) includes a detection antenna (receiving antenna) 32 configured to receive the electromagnetic wave, a detector side cable 15, which is connected to the detection antenna 32, and a detector (DET) 12, which is connected to the detector side cable 15 so that the detector 12 can be electrically connected to the detection antenna 32. The detector 12 detects information relating to the interface, the information is then carried by the electromagnetic wave.

The interface detection apparatus according to the first embodiment further embraces a data processor 13, which is connected to the detector 12 via a cable 16. The data processor 13 accepts the output signals from the detector 12, and execute a process along with a program based upon the accepted data to define an absolute position of the hidden interface with respect to a given reference position. The bottom of the container 34 may be assigned as the given reference position. The data processor 13 may encompass an interpreter, a compiler, and a run-time system, or another mechanism, together with the associated host computing machine and operating system, or another mechanism for detecting the hidden interface.

The traveling mechanism (45, 46) includes a z-axis traveling stage 45 supporting the detection antenna 32, which has a linear guiding mechanism (such as a V-groove guiding mechanism) configured to shift the relative position of the detection antenna 32 with respect to the container 34, along the z-axis (along the force of gravity when the x and y axes are the horizontal axes), and a z-axis driver 46 such as a step motor, a servomotor, a linear motor, an ultrasonic motor, an electrostriction device, or a magnetostriction device, which drives the z-axis traveling stage 45. An electrical position sensor for measuring an inductance or a capacitance, or an optical position sensor such as a laser interferometer, which is not shown in the drawings, should be added so as to achieve a highly accurate feedback control of positioning. Note that the traveling mechanism (45, 46) shown in FIG. 1A is an example. Alternatively, the detection antenna 32 may be fixed and the container 34 may be shifted as with an interface detection apparatus according to a third embodiment to be described later. In addition, a second z-axis traveling stage configured to shift the radiation antenna 31 along the z-axis simultaneously with the detection antenna 32, and a second z-axis driver, which drives the second z-axis traveling stage, may be provided, so that the detection antenna 32 is located on the same horizontal plane with the radiation antenna 31, in the direction of directivity of the radiation antenna 31.

Although there are no restrictions on the frequency of the electromagnetic waves used for the interface detection apparatus, according to the first embodiment of the present invention, in principle, as the frequency decreases, the size of the radiation antenna 31 and the detection antenna 32 becomes larger. As a result, the size of the interface detection apparatus becomes larger, making it inconvenient for the operator, or it becomes difficult to use as a measurement unit. More specifically, as the wavelength λ of the electromagnetic wave increases, the size of the detection antenna 32 must be made larger, resulting in degradation in resolution for position detection.

In general, when the first and second materials 41 and 42 are irradiated with electromagnetic waves, the first and second materials 41 and 42 absorb the electromagnetic wave energy. Therefore, consideration for a phenomenon of the electromagnetic waves being gradually damped while propagating through the first and second materials 41 and 42 is necessary.

(A) When Materials are Conductive:

In the far-field region (the Fraunhofer region), the propagation constant $\gamma_i$ (i=1, 2) is represented by the following equation when an electromagnetic wave propagates through the first material and the second material 41 and 42; where the first and second materials 41 and 42 are conductive dielectric materials:

$$\gamma_i = j\omega(\epsilon_i \mu_i)^{1/2} \{1 - j(\sigma_i/\omega\epsilon_i)\}^{1/2} \quad (1)$$

In the above Eq. (1), $\sigma_1$ denotes the conductivity of the first material 41, $\epsilon_1$ denotes the dielectric constant of the first material 41, and $\mu_1$ denotes the permeability of the first material 41. Further, $\sigma_2$ denotes the conductivity of the second material 42, $\epsilon_2$ denotes the dielectric constant of the second material 42, and $\mu_2$ denotes the permeability of the second material 42. $\omega = 2\pi f$ denotes an angular frequency. If we define a parameter of $p_i = \sigma_i/\omega\epsilon_i$, there is a case that the parameter $p_i$ satisfies $0.1 < p_i < 10$, for specific materials of the first and second material 41 and 42, although it may depend on physical properties of the first and second material 41 and 42. When the parameter $p_i$ satisfies $0.1 < p_i < 10$, the real part of Eq. (1) can be simplified and represented by attenuation constant $\alpha_i$ as the following equation:

$$\alpha_i \cong \omega[(\mu_i \epsilon_i/2)\{(1+p_i^2)^{1/2} - 1\}]^{1/2} \quad (2)$$

If the frequency f is high, Eq. (2) becomes $$\alpha_i \cong \omega\{(\mu_i \epsilon_i/2)p_i\}^{1/2} \quad (3)$$

A degree of penetration into the first and second materials 41 and 42 is represented by the attenuation length $\delta_i$ through which the power density is damped to $e^{-2}$. Here, the attenuation length $\delta_i$ is given by an inverse of attenuation constant $\alpha_i$, and is called a 'skin depth' or 'penetration depth' In the above Eq. (3), since $\delta_i = 1/\alpha_i$, the following equation $$\delta_i \cong (1/\pi f \mu_i \sigma_i)^{1/2} \quad (4)$$

can be approximately obtained. For example, when the dielectric constants of the first and second materials 41 and 42 are almost the same as that of water, and almost all of the molecules making up the first and second materials 41 and 42 can be considered to be nonmagnetic materials, it can be estimated (assumed) that $\epsilon_{ri} \cong 80$ [F/m], and $\mu_{ri} \cong 1$ [H/m]. The dielectric constant and the permeability in a vacuum are $\epsilon^0 \cong 8.8542 \times 10^{-12}$ [F/m], and $\mu_0 \cong 4\pi \times 10^{-7}$ [H/m], respectively. With the interface detection apparatus shown in FIG. 1, according to Eq. (4), $\delta_i$=approximately 70 µm when the first and second materials 41 and 42 are irradiated with electromagnetic wave of the frequency of 3 THz, and $\delta_i$=approximately 115 µm when the first and second materials 41 and 42 are irradiated with electromagnetic wave of the frequency of 1.2 THz. Therefore, measurement becomes difficult or the apparatus becomes complex and extremely large unless at least one of the thicknesses (geometric sizes) of the first and second materials 41 and 42 measured along the propagation direction of the electromagnetic wave is almost the same as the skin depth $\delta_i$.

(B) When Materials are Not Conductive:

When the first and second materials 41 and 42 are not conductive dielectric materials, a dielectric loss must be taken into account. The dielectric loss is represented by complex dielectric constant $\epsilon$. Although the normal dielectric constant is a real number, when the complex dielectric constant is used, the following equation is obtained.

$$\epsilon = \epsilon' - j\epsilon'' \quad (5)$$

where the real part indicates the normal dielectric constant, and the imaginary part indicates the loss. With these, the attenuation constant $\alpha$ of a plane wave, which propagates through a material in the far-field region (the Fraunhofer region), is obtained using the following equation.

$$\alpha \cong (\pi/\lambda) \cdot (\epsilon''/(\epsilon')^{1/2}) \quad (6)$$

Since $\epsilon'$ and $\epsilon''$ are functions of frequency, and not fixed, it is difficult to represent the attenuation constant $\alpha$ by an equation over a wide frequency range. On the other hand, within a frequency range that allows each of those values to be regarded as a nearly constant value, the greater the frequency to be used (the wavelength decreases accordingly), the greater the attenuation constant $\alpha$. Therefore, those values can be treated in the same way as the skin depth $\delta_i$ in Eq. (4), but the application of Eq. (6) to a general case for a wide band of frequencies may be difficult.

According to Eq. (6), as the frequency increases, the loss generally increases. Therefore, when there is a large loss, a high power transmitter of the electromagnetic wave is needed.

Strictly speaking, an exact analysis of electromagnetic wave propagation in a matter having an interface between the first and second materials 41 and 42, under the condition that the field from the antenna can be regarded to be near-field region (the Fresnel region), is necessary. However, it can be understood from the above discussion that the objective range of the wavelength λ is approximately determined based upon the physical properties and electrical sizes of the first and second materials 41 and 42 in the container 34. 'The electrical size' is measured in terms of the wavelength λ. If the first and second materials 41 and 42 are made of conductive materials, respectively, sub-millimeter waves and microwaves of less than 1 THz are preferable, considering the skin depth $\delta_i$. Note that as it is well known, microwaves include millimeter waves (extremely-high frequencies: EHF) of 30 GHz to 300 GHz, centimeter waves (super-high frequencies: SHF) of 3 GHz to 30 GHz, and ultra-high frequency (UHF) waves of 300 MHz to 3 GHz. If the first material 41 is made of a conductive material such as a liquid, and the second material 42 is made of nonconductive material such as air, electromagnetic waves of a terahertz band, visible light, ultraviolet-ray, or electromagnetic waves in further higher-frequency regions may be used.

If microwaves are used, high-frequency transmission lines, such as coaxial cables, rectangular waveguides, circular waveguides, microstrip lines, or coplanar waveguides may be used as the cables 14 and 15. Variable stubs for adjusting impedances of the high-frequency transmission lines, which are omitted in the drawings, may be provided to the cables 14 and 15. The coaxial detector side cable 15 is made from a flexible cable so that the traveling mechanism (45 and 46) can move the detection probe (detection antenna) 32 along the z-axis.

The data processor 13 is connected via the cable 16 to the detector 12 and records data such as the relationship of detected signals (electric power or phase) when the relative position of the detection probe (detection antenna) 32 is shifted in a certain direction (along the z-axis) with respect to the position of the sample (34, 35, 41, 42) (see FIGS. 2 through 6 to be described later), and it calculates based upon this data In addition, the data processor 13 outputs the control signal $S_{CNT}$ to the z-axis driver 46 to acquire this data. The z-axis driver 46 is controlled in conformity with the control signal $S_{CNT}$, so as to drive the z-axis traveling stage 45 shifting the relative position of the detection probe (detection antenna) 32 in a certain direction (along the z-axis) with respect to the position of the sample (34, 35, 41, 42). Note that the traveling mechanism (45, 46) shown in FIG. 1A is an example. Alternatively, as a more simplified architecture, multiple pedestals, each of which being configured to support the detection probe 32, with different heights may be prepared and a person (or an operator) may change stepwise the positions of the detection probe 32 by selecting corresponding heights of pedestals as needed for the position of the detection probe 32. Alternatively, a certain z-axis direction guiding mechanism may be provided to semi-automatically change the position using a screw (e.g., a ball screw) turning method, a rack-pinion driving method, or a friction driving method. If such a manual operation is included, the data processor 13 does not have to output the control signal $S_{CNT}$ to the z-axis driver 46; however, automatic control is naturally more preferable. In addition, the data processor 13 may also send a control signal to the oscillator 11 to control irradiation of the electromagnetic waves. In general, the cable 16 does not have to be a high-frequency transmission line.

If microwaves are used, microwave vacuum devices such as a magnetron, a traveling wave tube, a klystron, or a carcinotron (M-type backward oscillator); and microwave semiconductor devices such as monolithic microwave integrated circuits (MMICs) using Gunn diodes, impact-avalanche transit-time (IMPATT) diodes, tunnel injection transit-time (TUNNET) diodes, high electron mobility transistors (HEMTs), heterojunction bipolar transistors (HBTs), or ideal static induction transistors (SITs); or Josephson plasma excitation devices are available for the oscillator 11. A Schottky diode or a bolometer may be used as the detector 12. In addition, a low noise amplifier, which amplifies output signals from the Schottky diode or the bolometer, and/or a spectrum analyzer may be included in the detector 12. The Schottky diode or the bolometer and the low noise amplifier that implement the detector 12 may be monolithically integrated onto the same chip. In addition, miscellaneous logic circuits and memories configured to implement functions of the data processor 13 may also be monolithically integrated. Note that the frequencies of the electromagnetic waves used for the interface detection apparatus according to the first embodiment are not limited to those of microwaves, and various oscillators 11 and detectors 12 may be selected in accordance with the appropriate frequency of electromagnetic wave to be used.

Considering Eq. (4), a dielectric substance, which is transparent to electromagnetic waves having a specific measurement frequency, is used as the preferred material of the container 34. Various organic resin materials, or inorganic materials such as ceramic or glass are available for the material of the container 34. Phenol resin, polyester resin, epoxy resin, polyimide resin, fluorocarbon resin, or the like is available for the resin material. Alumina ($Al_2O_3$), mullite ($3Al_2O_3 \cdot 2SiO_2$), beryllium oxide (BeO), aluminum nitride (AlN), silicon nitride (SiC), or the like is available for the material of the ceramic container. Quartz glass, borosilicate glass, soda lime glass, or the like is available for the glass material. Note that naturally, the material of the container 34 is selected according to properties such as chemical reactivity with the first and second materials 41 and 42 to be contained therein.

The interface detection apparatus according to the first embodiment shown in FIG. 1A further includes a first anti-reflection plate 21, which is deployed on the irradiation mechanism (11, 14, 31) side, and a second anti-reflection plate 22, which is deployed on the detection mechanism (32, 15, 12) side; wherein the flat anti-reflection plates 21 and 22 face each other and sandwich the container 34. Various wave absorbers such as a coated wave absorber, which is made of a mixture of epoxy resin, titanium oxide, and carbon powder, a rubber wave absorber, which is made of synthetic rubber in which carbonyl iron is dispersed, a $\lambda/4$ wave absorber, or the like are available for the anti-reflection plates 21 and 22. Either a resonant-type or a matched-type $\lambda/4$ wave absorber is available. The first anti-reflection plate 21, which is deployed on the input side of the radiation antenna 31, and the second anti-reflection plate 22, which is deployed on the output side of the detection antenna 32, are used to reduce reflection of unnecessary electromagnetic waves in a measurement space. Therefore, the anti-reflection plates 21 and 22 are not essential for the interface detection apparatus according to the first embodiment, but they are effective in enhancing measurement accuracy and sensitivity.

Note that a detector side MMIC, in which Schottky diodes, low noise amplifiers, and impedance adjustment devices are monolithically integrated so as to implement the detector 12, may be mounted on the back side of the second anti-reflection plate 22, or the side not facing the radiation antenna 31 of the second anti-reflection plate 22. Hybrid integration provided by further mounting another semiconductor chip, or a plurality of semiconductor chips, each having various functions such as that of the data processor 13 on the back side of the second anti-reflection plate 22, can achieve a reduction in the size of the interface detection apparatus according to the first embodiment. In this case, an insulator substrate made of various kinds of organic synthetic resin, or inorganic materials such as ceramic or glass may be bonded to the back side of the second anti-reflection plate 22. In addition, a metal substrate may be contained, or a multi-layered metal-based substrate (a metal insulator substrate) may be provided by stacking a polyimide resin plate with high heat resistance on, for example, a metal such as iron (Fe) or copper (Cu) so that heat dissipation characteristics can be improved. A ceramic substrate such as $Al_2O_3$, BeO, or AlN, which has good heat dissipation, may be bonded to the back side of the second anti-reflection plate 22. Alternatively, a detector side semiconductor chip, in which Schottky diodes, low noise amplifiers, and the like implementing the detector 12 and the data processor 13 are all monolithically integrated and may be mounted on the insulator substrate, which is bonded to the back side of the second anti-reflection plate 22.

Similarly, an arrangement where a transmitter side semiconductor chip of MMIC, in which transmitter side semiconductor devices such as semiconductor amplifiers, and impedance adjustment devices are monolithically integrated so as to implement the oscillator 11, is mounted on the back side of the first anti-reflection plate 21, or the side not facing the detection antenna 32 of the first anti-reflection plate 21 and can achieve a reduction in the size of the interface detection apparatus according to the first embodiment.

Figure 1B:
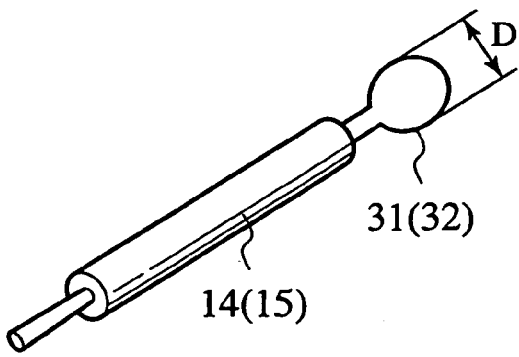
FIG. 1B is a schematic diagram for describing the detailed configuration of a loop antenna employed in the interface detection apparatus according to the first embodiment.

A loop antenna as shown in FIG. 1B is available for the radiation antenna (transmitting antenna) 31 and the detection antenna (receiving antenna) 32. As it is well known, within the far-field region, in which the field from the antenna is sufficiently far away from the distance of the order of the wavelength λ of the electromagnetic wave, the maximum power is radiated along the plane of the loop surface of the loop antenna, and the minimum power is radiated in the direction perpendicular to the loop surface. The loop length of the loop antenna to be used as the radiation antenna 31 should be almost the same as the resonance wavelength λ in order to enhance radiation efficiency. The size (loop length) of the loop antenna to be used as the detection antenna 32 should be the same as the resonance wavelength λ in order to enhance detection sensitivity; however, when the loop is large, the average electromagnetic wave in that space may be measured. Therefore, it is preferable that the electrical size of the detection antenna 32 is as small as possible so that the loop length can be less than λ/3 or λ/7 with a certain loop area, which allows reception of transmitted waves. A very electrically small loop antenna with a loop length of λ/10 is also available for the detection antenna 32. Therefore, in general, the electrical size of a loop antenna to be used as the radiation antenna 31 may differ from that of a loop antenna to be used as the detection antenna 32. In the case of higher frequencies such as sub-millimeter waves, or in the case of a small diameter of a circular loop antenna to be used as the detection antenna 32 being less than 1 mm, which is necessary to achieve high accuracy, a closed contour of the loop antenna should be delineated through photolithography at the end of a signal line formed as a conducting strip on the insulating substrate in which a microstrip line, a thin-film strip line, and a coplanar waveguide are formed.

There is no restriction on the shape of the loop antenna, and variously shaped loop antennas, such as circular, ellipsoidal, eccentric circular, rectangular, triangular (delta), rhombic, or polygonal with more sides than a pentagon, may be used connecting to the high-frequency transmission line such as the coaxial cable; wherein the polygon does not have to be a regular polygon. Alternatively, variously shaped antennas, such as circular, ellipsoidal, eccentric circular, rectangular, triangular, rhombic, or polygonal geometry, may be formed on a printed circuit board (PCB) or a printed wiring board (PWB). In addition, the geometry of a loop antenna to be used as the radiation antenna 31 does not have to be identical to that of a loop antenna to be used as the loop antenna 32.

Figure 1C:
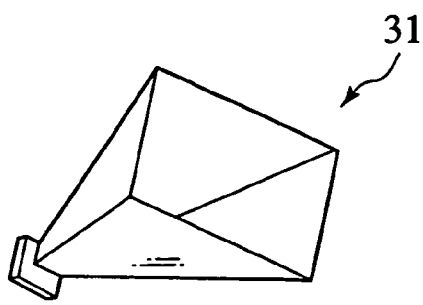
FIG. 1C is a schematic diagram for describing the detailed configuration of a pyramidal horn antenna employed in the interface detection apparatus according to the first embodiment.

Furthermore, besides the loop antenna, various antennas such as a horn antenna, a dipole antenna, an array antenna, a patch antenna may be used as the radiation antenna 31. FIG. 1C shows a pyramidal horn antenna as an example of the horn antenna, but the horn antenna is not limited to the pyramidal horn antenna as shown in FIG. 1C, and a sectoral H-plane antenna, a sectoral E-plane antenna, or a conical horn antenna may be used alternatively. A well-known example of the array antenna is Yagi antenna.

In the interface detection apparatus according to the first embodiment shown in FIG. 1A, the oscillator 11 radiates electromagnetic waves to the outside via the transmitter side cable 14, the first anti-reflection plate 21, and the radiation antenna (loop antenna) 31. The radiated electromagnetic waves from the radiation antenna 31 pass through the container 34 and the first and second materials 41 and 42 contained therein, and are then gathered by the detection antenna (loop antenna) 32. An output from the detection antenna 32 goes through the detector side cable 15 and then the second anti-reflection plate 22, and ends up being detected by the detector 12. The data processor 13 performs necessary data processing for identifying the absolute position of the hidden interface with the detected signal with respect to a given reference position.

As is found in Eq. (1), since the electromagnetic wave propagation constant $\gamma_i$ (i=1, 2) varies depending on the material constants such as conductivity $\sigma_i$, dielectric constant $\epsilon_i$, and permeability $\mu_i$, the hidden interface between the first material (i=1) 41 and the second material (i=2) 42 can be detected based upon the difference of the measured electromagnetic wave intensities. In other words, the traveling mechanism (45, 46) shift the relative positions of the detection antenna 32 with respect to the position of the container 34 so that the data processor 13 can compare each transmitted power level at each of the relative positions so as to identify the absolute position of the hidden interface between the first and second materials 41 and 42. In this case, the detection antenna 32 may be fixed and relative positions of the container 34 with respect to the detection antenna 32 may be shifted instead of shifting the relative positions of the detection antenna 32, as described above.

Note that the interface detection apparatus according to the first embodiment may identify the absolute position of the hidden interface between the first and second materials 41 and 42 by detecting the phase difference of the transmitted electromagnetic waves as well as detect the interface by measuring the transmitted power levels. According to the notation of the complex dielectric constant ε in Eq. (5), the phase constant β is defined as follows:

$$\beta \cong (2\pi/\lambda)(\epsilon')^{1/2} \qquad (7)$$

Therefore, the phase constant β of the electromagnetic wave changes depending on the dielectric constants ε' of the materials. Detection of this change (phase difference), or an amount of phase shift allows identification of the absolute position of the hidden interface between different materials and the identification of the absolute position of the hidden interface from the attenuation. More specifically, in the case where the dielectric constants of the first and second materials 41 and 42 are different from each other even when the medium loss for the first and second materials 41 and 42 are at the same level, phase detection of a transmitted electromagnetic wave is effective in detecting the hidden interface between the first and second materials 41 and 42.

As a result, materials to be used as the first and second materials 41 and 42 can be measured regardless of the sates of matter such as solid, liquid, or gas, by the interface detection apparatus according to the first embodiment. In other words, any combination of materials is possible as long as at least one of the constants $\sigma_i$, $\epsilon_i$, and $\mu_i$ for a measurement electromagnetic wave is different at the interface between the first and second materials 41 and 42.

In addition, the upper limit for the thickness (geometrical size) of the first and second materials 41 and 42, measured along a propagation direction of the electromagnetic wave is determined by the penetration depth $\delta_i$ prescribed by Eq. (4) or by the attenuation constant α prescribed by Eq. (6), so that the electromagnetic wave can propagate through the material and can be detected by an outer detection antenna 32. The lowest limit for the geometrical sizes of the first and second materials 41 and 42 is the sizes of the radiation antenna 31 and the detection antenna 32. Note that the above discussion is based upon a precondition that there are differences between the first and second materials 41 and 42 in terms of the constants $\sigma_i$, $\epsilon_i$, and $\mu_i$, which are large enough to distinguish interfaces.

Since the longer the distance between the radiation antenna 31 and the detection antenna 32 relative to the wavelength $\lambda$ of the electromagnetic wave, the interaction between the electromagnetic waves propagated through the first and second materials 41 and 42 becomes stronger, and becomes to be averaged, the output power change rate measured at the hidden interface between the first and second materials 41 and 42 decreases accordingly. Therefore, it is desirable for the measurement to be performed in the near-field region (the Fresnel region), in which the distance between the radiation antenna 31 and the detection antenna 32 is less than 15$\lambda$, or more preferably, less than 10$\lambda$, or still more preferably, less than 5$\lambda$, yet still more preferably, less than 3$\lambda$. This is equivalent to the condition that the distance between the irradiation mechanism (11, 14, 31) and the detection mechanism (32, 15, 12) is less than 15$\lambda$, or more preferably, less than 10$\lambda$, or still more preferably, less than 5$\lambda$, yet still more preferably, less than 3$\lambda$. 'The distance between the irradiation mechanism (11, 14, 31) and the detection mechanism (32, 15, 12)' is defined as 'the smallest distance measured between the irradiation mechanism (11, 14, 31) and the detection mechanism (32, 15, 12)' in the present specification. In the near-field region near the radiation antenna 31, the electromagnetic wave is regarded as a spherical wave.

On the other hand, since the longer the distance between the radiation antenna 31 and the detection antenna 32 relative to the wavelength $\lambda$, the lesser the affect from reflection developed between the radiation antenna 31 and the detection antenna 32, due to a standing wave decrease. Detection may become easier even with a low output change rate. Therefore, it is necessary to set the distance between the radiation antenna 31 and the container 34, the distance between the detection antenna 32 and the container 34, and the distance between the radiation antenna 31 and the detection antenna 32 for each objective material of the first and second materials 41 and 42.

In the interface detection apparatus according to the first embodiment, when a polarized wave that has the electric field vector perpendicular to the hidden interface between the first and second materials 41 and 42 (the magnetic field vector is parallel to the interface) is used, since the output power change rate measured at the interface becomes remarkable, it is preferable that an orientation of the plane of the radiation antenna 31 is selected so that the electric field vector of the electromagnetic wave can be perpendicular to the interface. Since the intensity of the transmitted electromagnetic wave slightly varies at the hidden interface between the first and second materials 41 and 42, a polarized wave that has the electric field vector parallel with the hidden interface between the first and second materials 41 and 42 (the magnetic field vector is perpendicular to the interface) can be used, and in this parallel configuration, the orientation of the plane of the radiation antenna 31 may be selected to be perpendicular to the interface so that the electric field vector of the electromagnetic wave becomes parallel to the interface.

An interface detection method according to the first embodiment can be executed by the following procedure, using the interface detection apparatus according to the first embodiment shown in FIG. 1A.

(a) The data processor 13 outputs a control signal $S_{CNT}$ to the z-axis driver 46. The z-axis driver 46 then drives the z-axis traveling stage 45 to shift the position of the detection antenna 32 to the initial position (for example, a position near the bottom of the container 34).

(b) Next, the oscillator 11 is driven to supply electromagnetic waves to the radiation antenna 31 via the transmitter side cable 14, passing through the first anti-reflection plate 21. The electromagnetic waves are then radiated from the radiation antenna 31 to the outside so as to irradiate the sample (34, 35, 41, 42).

(c) The electromagnetic waves radiated from the radiation antenna 31 propagate through the container 34 and either the first material 41 or the second material 42 contained therein (e.g., at the initial position, it is assumed that the electromagnetic wave propagates through the first material 41, for example). In other words, the electromagnetic waves propagated through the sample (34, 35, 41, 42) are gathered by the detection antenna 32. In addition, an output from the detection antenna 32 is transferred via the detector side cable 15, passing through the second anti-reflection plate 22, and ends up being detected by the detector 12. Necessary operations such as impedance adjustment or the like are performed so that the output of the detector 12 is maximum under this condition. Upon completion of those adjustment operations, the data processor 13 records the output from the detector 12 as a transmitted power at the initial position.

(d) Next, the data processor 13 outputs a control signal $S_{CNT}$ to the z-axis driver 46 to drive the z-axis traveling stage 45 so that the relative position of the detection antenna 32 is shifted (raised) a certain 'unit distance' (e.g., 'the unit distance' is selected so that it spans the range of 1 mm to 5 mm) along the z-axis with respect to the position of the sample (34, 35, 41, 42).

(e) Under the unit distance-shifted position, the electromagnetic waves transmitted from the oscillator 11 are then supplied to the radiation antenna 31, which then radiates the electromagnetic waves to the outside, thereby irradiating the sample (34, 35, 41, 42).

(f) The electromagnetic waves radiated from the radiation antenna 31 propagates through the sample (34, 35, 41, 42), and are then gathered by the detection antenna 32, the relative position of which has been shifted by the unit shift distance with respect to the position of the sample (34, 35, 41, 42). In addition, the detector 12 detects the output from the detection antenna 32, and the data processor 13 records it as a transmitted power at the unit distance-shifted position, and compares it with a reference power level.

(g) If the data processor 13 determines that the transmitted power at the unit distance-shifted position does not fall within the range of the reference power level, it outputs a control signal $S_{CNT}$ to the z-axis driver 46 to drive further the z-axis traveling stage 45 so that the relative position of the detection antenna 32 is further shifted (raised) by the unit shift distance along the z-axis with respect to the position of the sample (34, 35, 41, 42).

(h) Under a new unit distance-shifted position, electromagnetic waves from the oscillator 11 are then supplied to the radiation antenna 31, which then radiates them to the outside, thereby irradiating the sample (34, 35, 41, 42). The electromagnetic waves radiated from the radiation antenna 31 propagate through the sample (34, 35, 41, 42), and are then gathered by the detection antenna 32, the relative position of which has been shifted an additional unit distance, and the output from the detection antenna 32 ends up being detected by the detector 12. The data processor 13 records the output of the detector 12 as a transmitted power at the additional unit distance-shifted position, and then compares it with the reference power level.

(i) If the data processor 13 determines that the transmitted power at the additional unit distance-shifted position falls within the range of the reference power level, it identifies the position as the absolute position of the hidden interface between the first and second materials 41 and 42. Otherwise, if the data processor 13 determines that the transmitted power at the additional unit distance-shifted position does not fall within that range, it outputs the control signal $S_{CNT}$ to the z-axis driver 46 to drive further the z-axis traveling stage 45 so that the relative position of the detection antenna 32 is further shifted (raised) by the unit distance along the z-axis with respect to the position of the sample (34, 35, 41, 42), it repeats the above step (h), and determines whether or not the measured transmitted power falls within that range.

(j) The data processor 13 repeats the above step (i) until the measured transmitted power falls within the range of the reference power level, and finally identifies the absolute position of the hidden interface between the first and second materials 41 and 42 with respect to a reference position. The reference position may be freely selected such as the bottom of the container 34, for example. As described above, the data processor 13 detects the absolute position of the hidden interface between the first and second materials 41 and 42, with respect to the reference position, from the relationship between the relative position of the detection antenna 32 and the output signal from the detection mechanism (32, 15, 12) or the signal detected by the detector 12.

Since the best measurement condition is not always obtained through impedance adjustment in the above step (c), it is preferable that the impedance is adjusted in the following manner so that the difference of magnitudes between the output of the detector 12 corresponds to the transmitted power through the first material 41 only and that it can only be maximum through the second material 42:

(i) The container 34 is filled with only the first material 41, and the data processor 13 then outputs a control signal $S_{CNT}$ to the z-axis driver 46. The z-axis driver 46 drives the z-axis traveling stage 45 to shift the detection antenna 32 to an adjustment position (e.g., near the center of the container 34 along the z-axis). Next, the oscillator 11 is driven to supply the electromagnetic waves to the radiation antenna 31 via the transmitter side cable 14, passing through the first anti-reflection plate 21. The electromagnetic waves are then radiated from the radiation antenna 31 to the outside, irradiating the first material 41. The electromagnetic waves radiated from the radiation antenna 31 propagate through the first material 41 and are then gathered by the detection antenna 32. In addition, the output from the detection antenna 32 is transferred via the detector side cable 15, passing through the second anti-reflection plate 22, and is then detected by the detector 12.

(ii) Next, the container 34 is filled with only the second material 42, and the z-axis traveling stage 45 is driven to shift the detection antenna 32 to an adjustment position. Next, the electromagnetic waves from the oscillator 11 are supplied to the radiation antenna 31 via the transmitter side cable 14, passing through the first anti-reflection plate 21. The electromagnetic waves are then radiated from the radiation antenna 31 to the outside, irradiating the second material 42. The electromagnetic waves radiated from the radiation antenna 31 propagate through the second material 42, and are then gathered by the detection antenna 32. The output from the detection antenna 32 is transferred via the detector side cable 15, passing through the second anti-reflection plate 22, and ends up being detected by the detector 12. At this time, necessary processing, such as impedance adjustment, is performed so that the difference of the outputs from the detector 12 corresponding to the transmitted powers through the first and second materials 41 and 42, respectively, can be maximum. After the predetermined adjustment processing ends, the data processor 13 records the output from the detector 12, which has detected the transmitted powers through the first and second materials 41 and 42, as a reference transmitted power.

After this impedance adjustment is finished, the sample (34, 35, 41, 42) with an unknown absolute position of the interface, but containing the same materials of the first and second materials 41 and 42, may be prepared, and measurement may begin from the above step (a). During this impedance adjustment process, the 'reference power level', which is a criterion of determination of the hidden interface between the first and second materials 41 and 42, may also be calculated. For example, the reference power level when the hidden interface between the first and second materials 41 and 42 is irradiated with electromagnetic waves can be calculated by pre-storing in the memory of the data processor 13 the reference transmitted power level detected when the container 34 is filled with only the first material 41, and the reference transmitted power level detected when the container 34 is filled with only the second material 42.

Alternatively, as a preliminary test, a specific transmitted power level is obtained as the reference power level beforehand, using a known position of the interface between the first and second materials 41 and 42 of the reference sample, irradiating with the electromagnetic waves on to the known position of the interface of the reference sample. The specific transmitted power level obtained in the preliminary test by the reference sample is then pre-stored as the reference power level in the memory of the data processor 13.

According to the interface detection apparatus and method of the first embodiment, the absolute position of the hidden interface of materials contained in the container 34, with respect to a reference position, can be measured externally without making contact with them when the container 34 is opaque or has an opaque seal such as paper attached to the surface thereof even if the container 34 is transparent. As is found in the results shown in the following FIGS. 2 through 6, the absolute position of the interface can be identified with an accuracy of less than $\lambda/10$, and using a higher frequency of electromagnetic waves can achieve improvement in resolution.

[When a Loop Antenna is Used as a Radiation Antenna]

Figure 2:
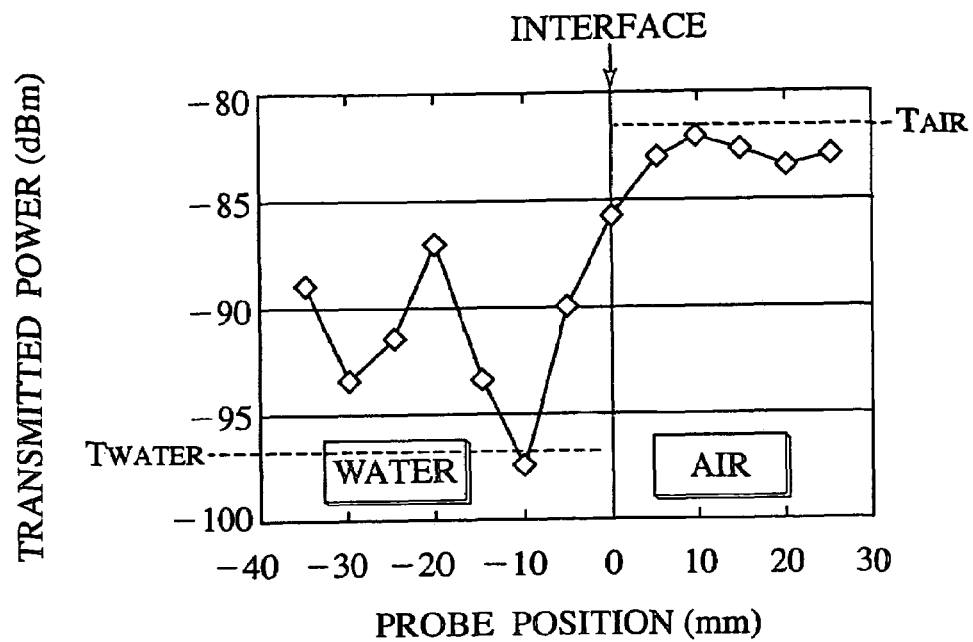
FIG. 2 is a diagram, according to the first embodiment, that shows the relationship between the transmitted power and the position of a detection antenna when irradiating with an electromagnetic wave from a loop antenna, the hidden interface between water and air using water as a first material, and air as a second material.
Figure 3:
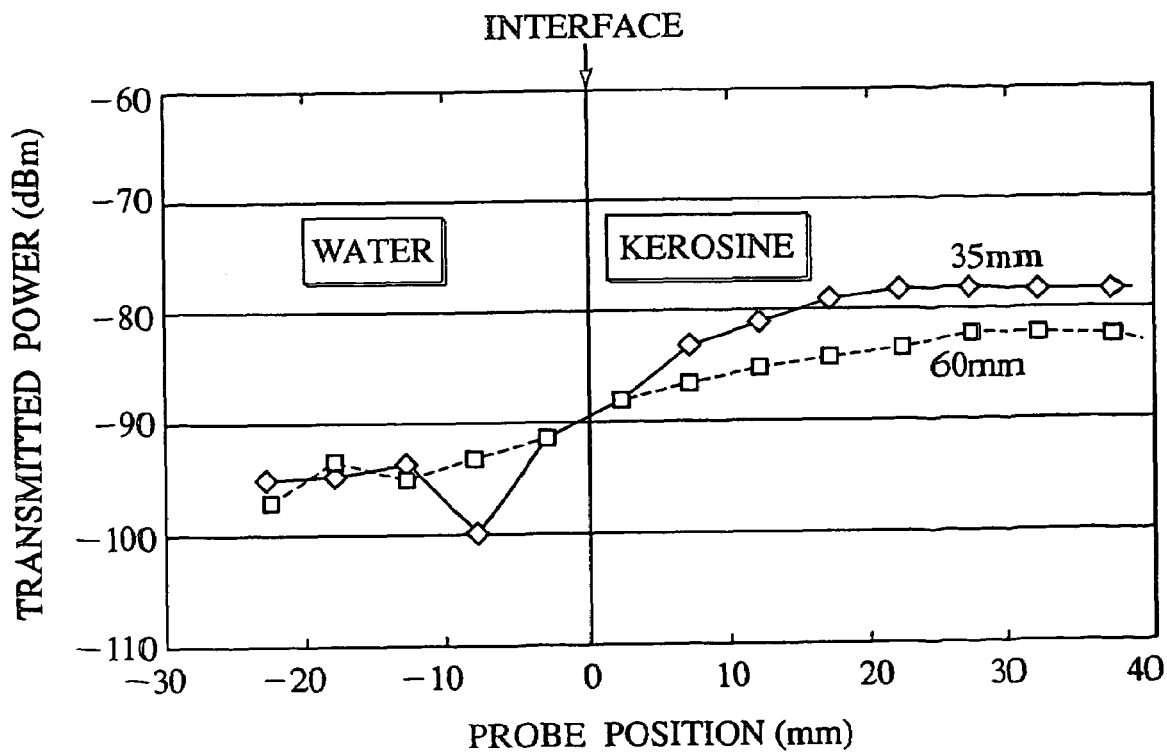
FIG. 3 is a diagram, according to the first embodiment, that shows the relationship between the transmitted power and the position of a detection antenna when irradiating with an electromagnetic wave from a loop antenna, the hidden interface between water and kerosene using water as a first material and kerosene as a second material.

FIG. 2 shows the relationship between the transmitted power detected by the detection antenna 32 and the relative position of the probe (detection antenna) 32 with respect to the container 34 along the z-axis when water and air are used as the first and second materials 41 and 42, respectively, and the hidden interface between water and air is irradiated with a 9.4-GHz electromagnetic wave. Note that as described above, there is no restriction in principle on the frequency of electromagnetic waves to be used for the interface detection apparatus, according to the first embodiment of the present invention, and the frequency of 9.4 GHz is merely an example. The relative position of the detection antenna with respect to the container 34 shown in the abscissa is measured along the z-axis, and the origin is set to the position of the hidden interface between the first and second materials 41 and 42. As already mentioned, the traveling mechanism (45, 46) shown in FIG. 1A is an example, and the data shown in FIGS. 2 and 3 are obtained under the condition such that the positions of the detection antenna 32 and the radiation antenna 31 are fixed and the position of the container 34 is shifted along the z-axis. In this case, since the hidden interface between the first and second materials 41 and 42 convexly curves downward due to the surface tension thereof as shown in FIG. 1A, there is a certain ambiguous zone (error) of the interface according to the curved portion. Note that the container 34 is a test tube made of borosilicate glass 16.5 mm in outer diameter, 1 mm in thickness, and 165 mm in length (the size and the material of the container 34 should be selected considering the conductivity $\sigma_i$, the dielectric constant $\epsilon_i$, and the permeability $\mu_i$, which define the propagation constant $\gamma_i$ in Eq. (1); however, the container 34 is not limited to being a test tube. All results shown in FIGS. 3 through 6, 8, and 9 are obtained using test tubes made of the same material with the same size as the container 34.)

In a free space, the frequency of 9.4 GHz corresponds to wavelength $\lambda$=3.2 cm. As described above, the diameter D of the loop antenna is determined based upon the relationship between the detection resolution and the detectable power level. In FIG. 2, the loop antenna 6 mm in diameter D (circumference length of the loop: 0.59 $\lambda$) is used as the radiation antenna 31, and the loop antenna 1.5 mm in diameter D (circumference length of the loop: 0.15 $\lambda \approx \lambda/7$) is used as the detection antenna 32, as an example. Measurement in the near-field region (the Fresnel region) where the distance between the radiation antenna 31 and the detection antenna 32 is 35 mm ($\approx$1.1 $\lambda$), and the distance between the detection antenna 32 and the container 34 is 3 mm ($\approx$0.09 $\lambda$) is performed. Here, 'the distance between the detection antenna 32 and the container 34' is defined as 'the distance between the tip of the detection antenna 32 and the outer wall of the container 34'.

As shown in FIG. 2, comparing the transmitted power level with the reference power level, the absolute position of the hidden interface between the first and second materials 41 and 42 is identified. For example, as a preliminary test, a transmitted power level $T_{water}$, which is detected when the container 34 is filled with only the first material 41 of water, and a transmitted power level $T_{air}$, which is detected when the container 34 is filled with only the second material 42 of air, are pre-stored in the memory of the data processor 13 in FIG. 1, and the reference power level when the hidden interface between the first and second materials 41 and 42 is irradiated with electromagnetic waves and then is calculated from the values: $T_{water}$ and $T_{air}$. Alternatively, as a preliminary test, the transmitted power level when the hidden interface between the first and second materials 41 and 42 is irradiated with electromagnetic waves and pre-stored as a reference power level in the memory of the data processor 13, the position of the interface should then be identified based upon that value.

As is found in FIG. 2, if a higher power than the reference power level is received, the detection antenna 32 is considered to be positioned in a region corresponding to air layer (second material) 42; otherwise if a lower (weaker) power than −86 dBm is received, the detection antenna 32 is considered to be positioned in a region corresponding to water layer (first material) 41. As a result, the hidden interface between the first and second materials 41 and 42 can be identified. In FIG. 2, setting the reference power level to −86 dBm can achieve identification of the absolute position of the hidden interface between the first and second materials 41 and 42 in approximately 3 mm to 1 mm ($\approx \lambda/10$ to $\lambda/30$) resolution. Usage of high frequency of electromagnetic waves can achieve identification in less than 1 mm resolution.

FIG. 3 shows the relationship between the transmitted power detected by the detection antenna 32 and the relative position of the probe (detection antenna) 32 along the z-axis with respect to the container 34 when water is used as the first material 41, kerosine is used as the second material 42, and the hidden interface between water and kerosine is irradiated with a 9.4-GHz electromagnetic wave. The origin along the abscissa indicates the position of the hidden interface between the first and second materials 41 and 42. In this case, since the hidden interface between the first and second materials 41 and 42 convexly curves downward due to the surface tension as shown in FIG. 1A, there is a certain ambiguous zone (error) of the position of the interface according to the curved portion.

In FIG. 3, the loop antenna 6 mm in diameter D is used as the radiation antenna 31, and the loop antenna 1.5 mm in diameter D is used as the detection antenna 32, as an example. Here, the diameter D of the loop antenna is determined based upon the relationship between the detection resolution and the detectable power level. The distance between the radiation antenna 31 and the detection antenna 32 is either 35 mm ($\approx$1.1 $\lambda$) or 60 mm ($\approx$1.9 $\lambda$), and the distance between the detection antenna 32 and the container 34 is 10 mm ($\approx$0.31 $\lambda$).

As with FIG. 2, it can be found in FIG. 3 that the absolute position of the hidden interface between the first and second materials 41 and 42 may also be identified based upon the transmitted power level. In this case, the shorter the distance between the radiation antenna 31 and the detection antenna 32, the more the interface resolution is miniaturized. It can be found in FIG. 3 that the longer the distance between the probe (detection antenna) 32 and the container 34, the smaller the variation of the transmitted power near the interface, however the effect due to the difference of the distances is small within the range of approximately 35 to 60 mm

[When a Horn Antenna is Used as a Radiation Antenna]

Figure 4:
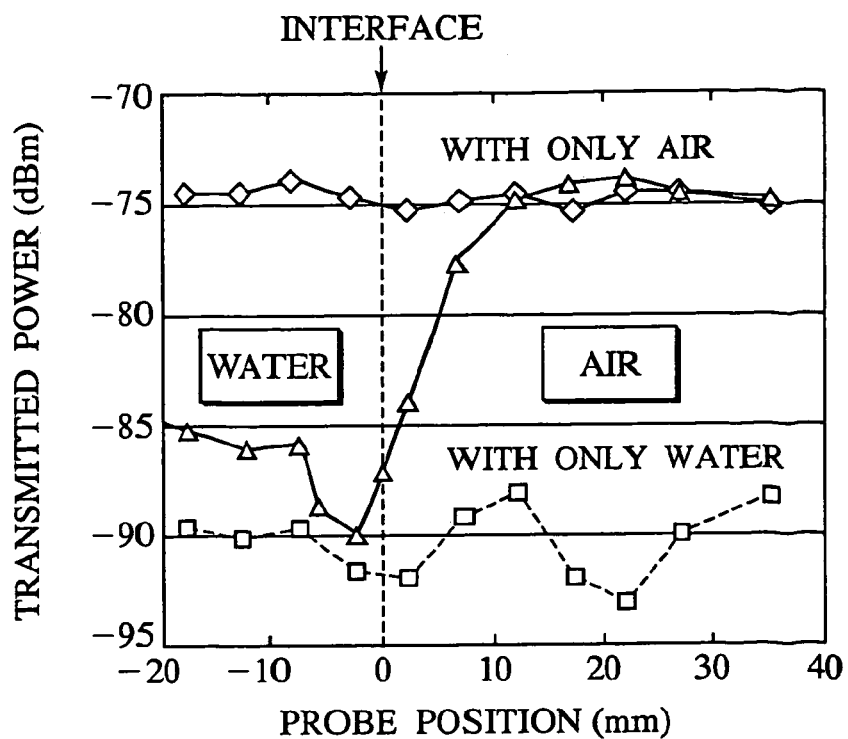
FIG. 4 is a diagram, according to the first embodiment, that shows the relationship between transmitted powers and positions of a detection antenna when irradiating with an electromagnetic wave from a horn antenna, the hidden interface between water and air using water as a first material and air as a second material.
Figure 5:
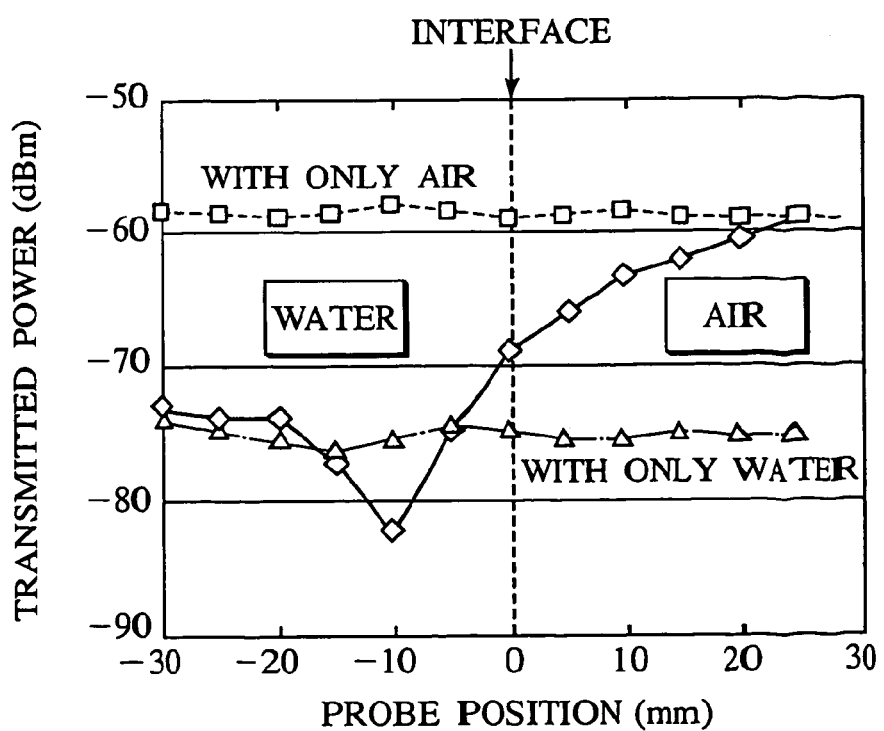
FIG. 5 is a diagram, according to the first embodiment, that shows the relationship between the position of a detection antenna and the transmitted power, which is detected by a loop antenna longer in diameter than that in FIG. 4 when irradiating with an electromagnetic wave from a horn antenna, the hidden interface between water and air using water as a first material and air as a second material.
Figure 6:
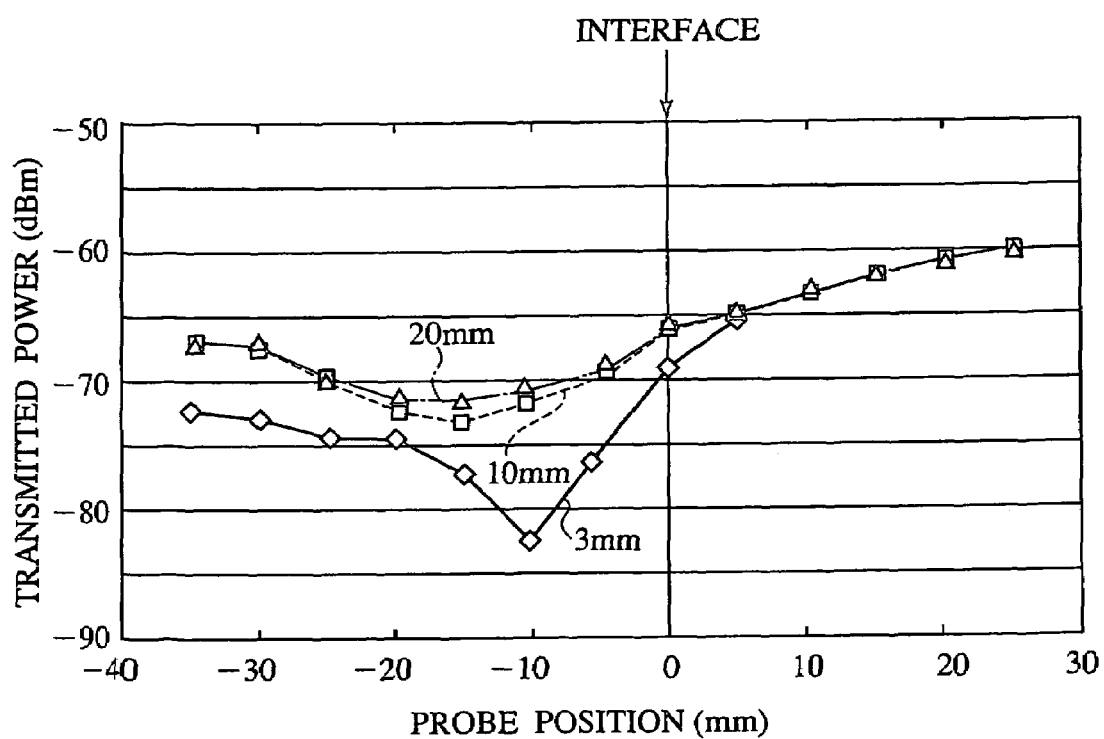
FIG. 6 is a diagram, according to the first embodiment, that shows the relationship between the transmitted power and the position of a detection antenna when irradiating with an electromagnetic wave from a horn antenna, the hidden interface between water and air using water as a first material and air as a second material while changing the distance between the detection antenna and a container to 3 mm (◇), 10 mm (□), and then 20 mm (△).

FIG. 4 shows the results from irradiating a 9.4-GHz electromagnetic wave using a pyramidal horn antenna as the radiation antenna 31. In this case, a loop antenna 1.5 mm in diameter D is used as the detection antenna 32. As described above, since the diameter D of the loop antenna is determined based upon the relationship between the detection resolution and the detectable power level, the diameter D is not necessarily 1.5 mm. Similarly to the measurement condition by which the data shown in FIGS. 2 and 3 are obtained, the data shown in FIGS. 4 to 6 are obtained under the condition such that the positions of the detection antenna 32 and the radiation antenna 31 are fixed and the position of the container 34 is shifted along the z-axis.

The measurement condition in which water is used as the first material 41, air is used as the second material 42, and the distance between the container 34 and the probe (detection antenna) 32 is approximately 3 mm ($\approx$0.09 $\lambda$), is the same as that of FIG. 2. FIG. 4 shows the relationship between the transmitted power detected by the detection antenna 32 and the relative position of the probe (detection antenna) 32 with respect to the container 34, which is indicated by a 'Δ' symbol, when irradiated with a 9.4-GHz electromagnetic wave, the position of the hidden interface between water and air, which is assigned to the container position of 0 mm. In addition, FIG. 4 shows: the relationship between the transmitted power and the relative position of the probe (detection antenna) 32 with respect to the container 34 when the container 34 is empty (i.e., the container 34 is filled with only the second material 42 of air) using a '◇' symbol, and the relationship between the transmitted power and the relative position of the probe (detection antenna) 32 with respect to the container 34 when the container 34 is filled with only water (i.e., the container 34 is filled with only the first material 41 of water) using a '□' symbol. In this case, since the hidden interface between the first and second materials 41 and 42 convexly curves downward due to the surface tension as shown in FIG. 1A, there is a certain ambiguous zone (error) in the position of the interface according to the curved portion as is the case with FIG. 2.

When a rectangular horn antenna (pyramidal horn antenna) is used as the radiation antenna 31, the accuracy is lower than when using the loop antenna as the radiation antenna 31 in FIG. 2; however, as shown in FIG. 4, the position of the hidden interface between the first and second materials 41 and 42 can be identified from the curve that indicates a variation in the transmitted power level. In other words, the transmitted power level (□), which is detected when the container 34 is filled with only the first material (water) 41, and the transmitted power level (◇), which is detected when the container 34 is filled with only the second material (air) 42, is pre-stored in the memory of the data processor 13, and allows the calculation of the reference power level when irradiating the hidden interface between the first and second materials 41 and 42 with an electromagnetic wave. Alternatively, the preliminary measurement results shown in FIG. 4 are used as calibration curves; the transmitted power level when irradiating the hidden interface between the first and second materials 41 and 42 with an electromagnetic wave is pre-stored as a reference power level in the memory of the data processor 13; and the value of that power level is used to identify the position of the interface.

As found in FIG. 4, the transmitted power varies at around the hidden interface between the first and second materials 41 and 42. It can be found that the magnitude of variation depend on the electromagnetic wave characteristics of the materials implementing the hidden interface between the first and second materials 41 and 42, and the physical properties of the materials can be represented by a curve showing the variation of the transmitted powers.

FIG. 5 shows the results when irradiating a 9.4-GHz electromagnetic wave using the pyramidal horn antenna as the radiation antenna 31 and also using a loop antenna 6 mm in diameter D, which is larger than that in FIG. 4, as the detection antenna 32 as is the case with FIG. 4. The distance between the detection antenna 32 and the container 34 is 3 mm ($\cong 0.09\ \lambda$) as is the case with FIG. 4. In FIG. 5, the transmitted power level ($\Delta$), which is detected when the container 34 is filled with only the first material (water) 41, and the transmitted power level (□), which is detected when the container 34 is filled with only the second material (air) 42, are pre-stored in the memory of the data processor 13, which allows the calculation of the reference power level when irradiating the hidden interface between first and second materials 41 and 42 with an electromagnetic wave. Alternatively, the preliminary measurement results shown in FIG. 5 are used as calibration curves; the transmitted power level found when irradiating the hidden interface between the first and second materials 41 and 42 with an electromagnetic wave is pre-stored as a reference power level in the memory of the data processor 13; and that reference power level may be used to identify the position of the interface.

FIG. 6 shows the results from irradiating a 9.4-GHz electromagnetic wave using a loop antenna 6 mm in diameter D as the detection antenna 32 as is the case with FIG. 4. In FIG. 6, the distance between the detection antenna 32 and the container 34 is changed to 3 mm ($\cong 0.09\ \lambda$) (◇), 10 mm ($\cong 0.31\ \lambda$) (□), and then 29 mm ($\cong 0.63\ \lambda$) ($\Delta$), so as to examine the effectiveness. When the distance between the detection antenna 32 and the container 34 is 3 mm ($\cong 0.09\ \lambda$), detection accuracy increases; otherwise when the distance between the detection antenna 32 and the container 34 is wider than 10 mm ($\cong 0.31\ \lambda$), the detection accuracy decreases. Note that it can be found that the degree of reduction in detection accuracy when the distance is 10 mm ($\cong 0.31\ \lambda$) or wider indicates almost saturation.

According to the interface detection apparatus and method of the first embodiment of the present invention, the absolute position of the hidden interface of materials in an optically opaque environment may be detected externally without making contact with them.

Second Embodiment

Figure 7:
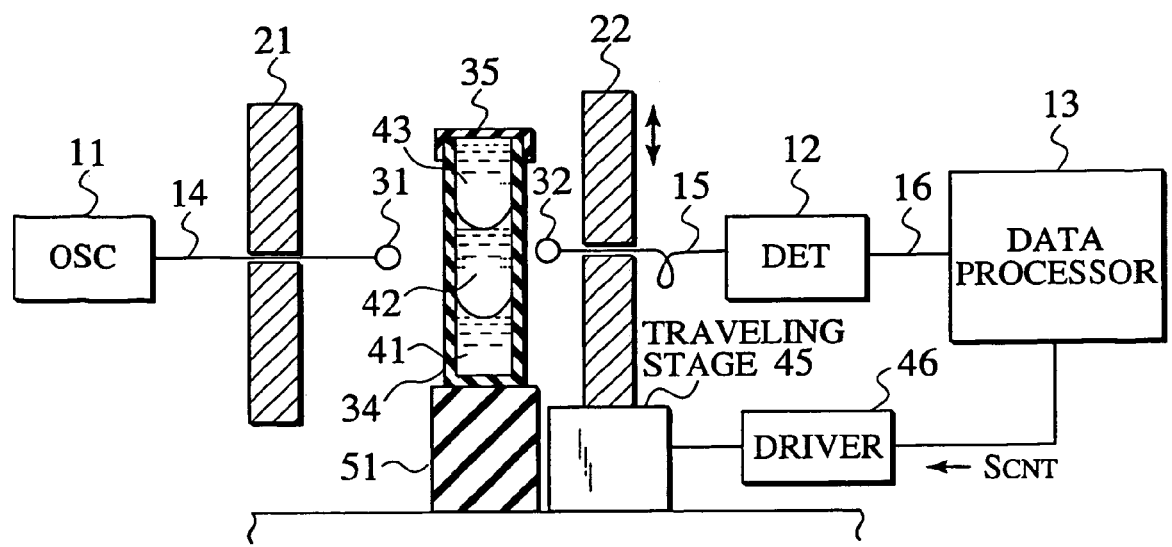
FIG. 7 is a schematic diagram for describing the configuration of an interface detection apparatus according to a second embodiment of the present invention.

As shown in FIG. 7, in an interface detection apparatus according to a second embodiment of the present invention, a sample (34, 35, 41, 42, 43) is implemented by a first material 41, a second material 42 and a third material 43 contained in container 34. Then, a first hidden interface is formed between the first and second materials 41 and 42, and a second hidden interface is formed between the second and third materials 42 and 43. The physical properties (material constants) $\sigma_i$, $\epsilon_i$, and $\mu_i$ (i=1, 2) for the first and second materials 41 and 42 are different from each other, and the physical properties (material constants) $\sigma_i$, $\epsilon_i$, and $\mu_i$ (i=2, 3) for the second and third materials 42 and 43 are different from each other.

That is, the interface detection apparatus according to the second embodiment of the present invention encompasses an irradiation mechanism (11, 14, 31), which irradiates electromagnetic waves onto a sample (34, 35, 41, 42, 43) having the first and second hidden interfaces, a detection mechanism (32, 15, 12), which detects electromagnetic waves that have passed through the sample (34, 35, 41, 42, 43), and a traveling mechanism (45, 46), which changes the relative position of the first and second hidden interfaces of the materials with respect to the detection mechanism (32, 15, 12). The container 34 has a lid 35 that seals this container 34. Generally, the lid 35 does not have to completely seal the container 34. As stated in the first embodiment, the lid 35 may be omitted according to circumstances or measurement specifications.

In the interface detection apparatus according to the second embodiment, the irradiation mechanism (11, 14, 31) includes an oscillator 11, a transmitter side cable 14, which is connected to the oscillator 11, and a radiation antenna (transmitting antenna) 31, which is connected to the transmitter side cable 14. In addition, the detection mechanism (32, 15, 12) includes a detection antenna (receiving antenna) 32, a detector side cable 15, which is connected to the detection antenna 32, and a detector 12, which is connected to the detector side cable 15. Similarly to the interface detection apparatus of the first embodiment, the interface detection apparatus according to the second embodiment shown in FIG. 7 further includes a first anti-reflection plate 21, which is deployed on the irradiation mechanism (11, 14, 31) side, and a second anti-reflection plate 22, which is deployed on the detection mechanism (32, 15, 12) side; wherein the flat anti-reflection plates 21 and 22 face each other and sandwich the container 34.

The traveling mechanism (45, 46) includes a z-axis traveling stage 45 mounting the second anti-reflection plate 22, which has a linear guiding mechanism configured to shift the position of the second anti-reflection plate 22 along the z-axis, and a z-axis driver 46 configured to drive the movement of the z-axis traveling stage 45. By moving the position of the second anti-reflection plate 22 along the z-axis by the z-axis traveling stage 45, the relative position of the detection antenna 32 fixed to the second anti-reflection plate 22 moves along the z-axis with respect to the position of the container 34. A portion of the detector side cable 15 between the second anti-reflection plate 22 and the detector 12 is made of a flexible cable so that the position of the detection antenna 32 can travel freely along the z-axis while maintaining the position of the detector 12 at a fixed position. On the contrary, a perpendicularly protruding end portion of the detector side cable 15 from the surface plane of the second anti-reflection plate 22, disposed between the sample (34, 35, 41, 42, 43) and the second anti-reflection plate 22, is made of a nonflexible cable so that the vertical position of the tip of the detection antenna 32 can be rigidly determined by the vertical position of the second anti-reflection plate 22.

Note that the traveling mechanism (45, 46) shown in FIG. 7 is an example. Alternatively, the detection antenna 32 may be fixed and the relative position of the container 34 may be shifted as with an interface detection apparatus according to a third embodiment to be described later. In addition, a second z-axis traveling stage mounting the radiation antenna 31, configured to shift the radiation antenna 31 along the z-axis simultaneously with the detection antenna 32, and a second z-axis driver, which drives the second z-axis traveling stage, may be provided, such as that the detection antenna 32 is located on a horizontal plane aligned in the direction of directivity of the radiation antenna 31.

The detection antenna 32 is connected to the data processor 13 through a cable 16. The data processor 13 calculate a first reference power level for the first hidden interface between the first and second materials 41 and 42, when the first hidden interface is irradiated with electromagnetic waves, by pre-storing in the memory of the data processor 13 the reference transmitted power level detected when the container 34 is filled with only the first material 41, and the reference transmitted power level detected when the container 34 is filled with only the second material 42. The data processor 13 further calculate a second reference power level for the second hidden interface between the second and third materials 42 and 43, when the second hidden interface is irradiated with electromagnetic waves, by pre-storing in the memory of the data processor 13 the reference transmitted power level detected when the container 34 is filled with only the second material 42, and the reference transmitted power level detected when the container 34 is filled with only the third material 43.

Figure 8:
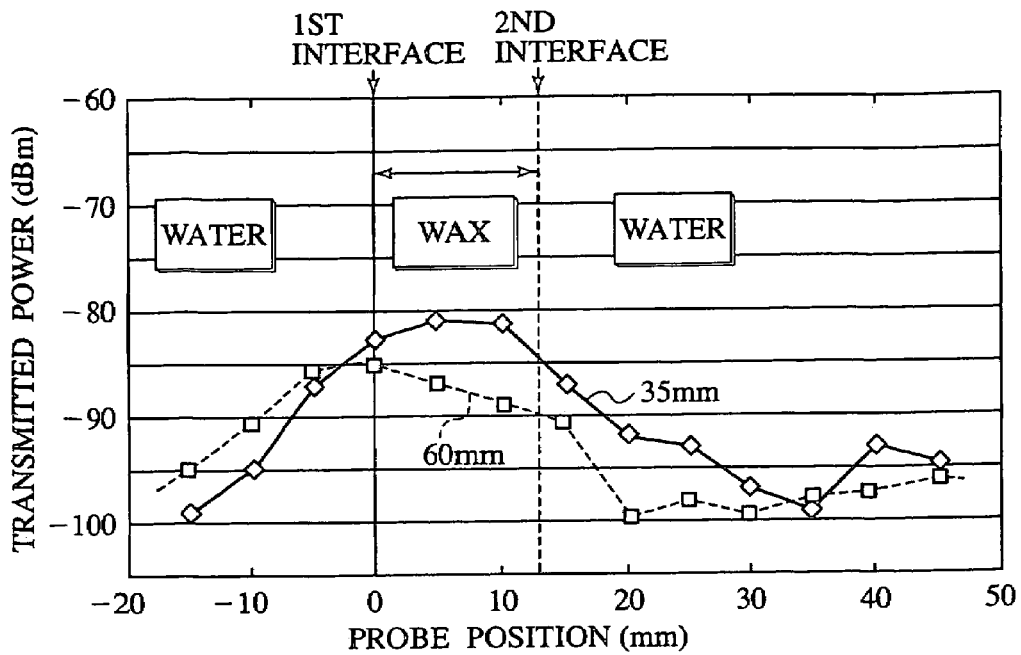
FIG. 8 is a diagram, according to the second embodiment, that shows the relationship between the transmitted power and the position of a detection antenna when irradiating with an electromagnetic wave from a loop antenna, with a first hidden interface between water and wax using water as a first material and wax as a second material, and a second hidden interface between wax and water using water as a third material.
Figure 9:
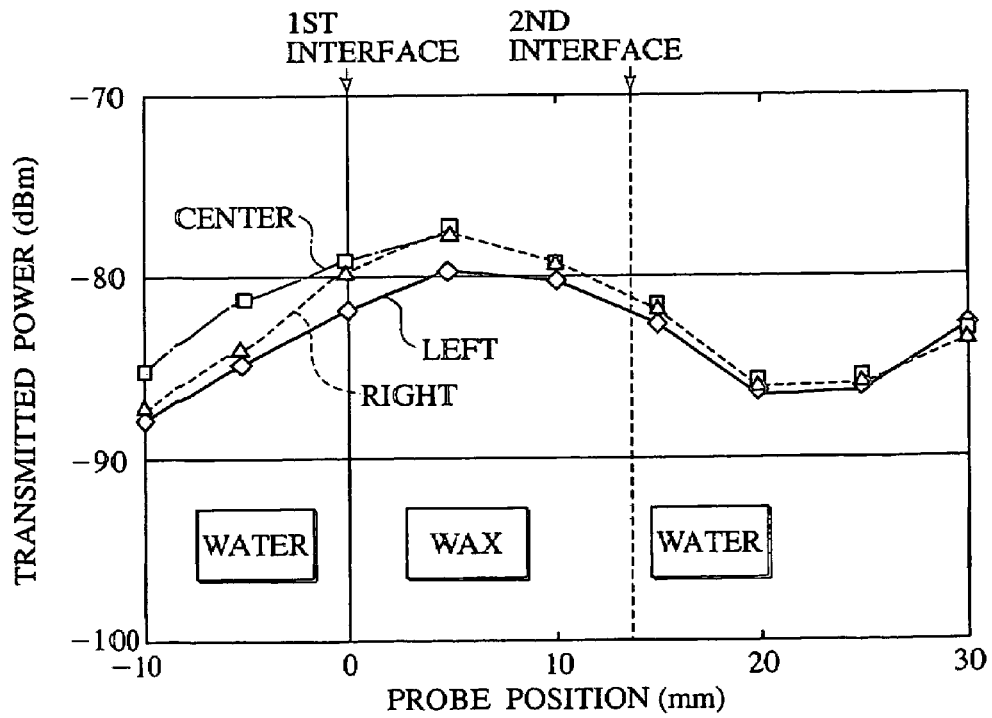
FIG. 9 is a diagram, according to the second embodiment, that shows the relationship between transmitted powers and positions of a detection antenna when irradiating with an electromagnetic wave from a horn antenna, with a first hidden interface between water and oil using water as a first material and the oil as a second material, and a second hidden interface between oil and water using water as a third material.

Or, the data processor 13 records data such as the relationship of detected signals (electric power or phase) when the relative position of the detection probe (detection antenna) 32 is shifted in a certain direction (along the z-axis) with respect to the position of the sample (34, 35, 41, 42, 43), and calculates the first and second reference power levels based upon these data. Namely, as a preliminary test, calibration curves such as those shown in FIGS. 8 and 9 are obtained so that a first specific transmitted power level when the first hidden interface between the first and second materials 41 and 42 is irradiated with electromagnetic waves and pre-stored as the first reference power level, and a second specific transmitted power level when the second hidden interface between the second and third materials 42 and 43 is irradiated with electromagnetic waves and pre-stored as the second reference power level in the memory of the data processor 13. Or, the data processor 13 may calculate the first reference power level for the first hidden interface and the second reference power level for the second hidden interface by derivatives, quadratic derivatives, or third derivatives of the curves showing relationships between transmitted powers (dBms) and probe positions, and may store the first and second reference power levels into the memory of the data processor 13.

In addition, the data processor 13 outputs the control signal $S_{CNT}$ to the z-axis driver 46 so as to shift the relative position of the probe, configured to acquire the curves showing relationships between transmitted powers and probe positions. The z-axis driver 46 is controlled in conformity with the control signal $S_{CNT}$, so as to drive the z-axis traveling stage 45 shifting the relative position of the second anti-reflection plate 22 in a certain direction (along the z-axis) with respect to the position of the sample (34, 35, 41, 42, 43). By moving the relative position of the second anti-reflection plate 22 along the z-axis by the z-axis traveling stage 45, the relative position of the detection antenna 32 moves along the z-axis. In addition, the data processor 13 may also send a control signal to the oscillator 11 to control irradiation of the electromagnetic waves.

Except for the organization of the traveling mechanism (45, 46) and the sample (34, 35, 41, 42, 43), embracing triple layer configuration with the first material 41, the second material 42 and the third material 43 contained in the container 34 so as to implement the first hidden interface between the first and second materials 41 and 42, and the second hidden interface between the second and third materials 42 and 43, other structures and materials are similar to the structure and materials already explained in the first embodiment, and overlapping or redundant descriptions may be omitted in the second embodiment.

The loop antenna as shown in FIG. 1B is available for the radiation antenna 31 and the detection antenna 32. Furthermore, besides the loop antenna, various antennas such as a horn antenna, a dipole antenna, an array antenna, a patch antenna may be used as the radiation antenna 31. The horn antenna is not limited to the pyramidal horn antenna as shown in FIG. 1C, and a sectoral H-plane antenna, a sectoral E-plane antenna, or a conical horn antenna may be used alternatively, although the illustrations are omitted.

In the interface detection apparatus according to the second embodiment shown in FIG. 7, the oscillator 11 radiates electromagnetic waves to the outside via the transmitter side cable 14, the first anti-reflection plate 21, and the radiation antenna (loop antenna) 31. The radiated electromagnetic waves from the radiation antenna 31 propagate through the container 34 and the first, second or third materials 41, 42 or 43 contained therein, and are then gathered by the detection antenna (loop antenna) 32. An output from the detection antenna 32 goes through the detector side cable 15 and then the second anti-reflection plate 22, and ends up being detected by the detector 12. The data processor 13 performs certain data processing for determining the absolute positions of the first and second hidden interfaces with the detected signal.

As is found in Eq. (1), since the electromagnetic wave propagation constant $\gamma_i$ (i=1, 2, 3) varies depending on the material constants such as conductivity $\sigma_i$, dielectric constant $\epsilon_i$, and permeability $\mu_i$, the first and second hidden interfaces between the first material (i=1) 41, the second material (i=2) 42 and the third material (i=3) 43 can be detected based upon the difference of the measured electromagnetic wave intensities or phases. The traveling mechanism (45, 46) can detect the first hidden interface between the first and second materials 41 and 42 or the second hidden interface between the second and third materials 42 and 43 by shifting the relative position of the detection antenna 32 and comparing each transmitted power level at each relative position. In this case, the detection antenna 32 may be fixed and the relative position of the container 34 may be shifted instead of shifting the detection antenna 32, as described above.

In this way, according to the interface detection apparatus and method of the second embodiment, the first and second hidden interfaces of materials contained in container 34 can be measured externally without making contact with them, when the container 34 is opaque or has an opaque seal such as paper attached to the surface thereof even if the container 34 is transparent. As is found in the results shown in the following FIGS. 8 and 9, the absolute positions of the first and second hidden interfaces implemented by triple layered materials can be identified with an accuracy of less than $\lambda/10$.

[When a Loop Antenna is Used as a Radiation Antenna]

FIG. 8 shows the relationship between the transmitted power detected by the detection antenna 32 and the relative position of the probe (detection antenna) 32 with respect to the container 34 along the z-axis when water, wax and water are used as the first, second and third materials 41, 42 and 43, respectively, and the first hidden interface between water and wax, or the second hidden interface between wax and water is irradiated with a 9.4-GHz (wavelength $\lambda=3.2$ cm) electromagnetic wave.

The relative position of the detection antenna with respect to the container 34 shown in the abscissa is measured along the z-axis, and the origin (z=0 mm) is assigned to the position of the first hidden interface, and z=15 mm is assigned to the position of the second hidden interface. As explained above, the traveling mechanism (45, 46) shown in FIG. 7 is an example, and the data shown in FIG. 8 is obtained under the condition such that the positions of the detection antenna 32 and the radiation antenna 31 are fixed and the position of the container 34 is shifted along the z-axis. In this case, since the first hidden interface between the first and second materials 41 and 42, and the second hidden interface between the second and third materials 42 and 43 convexly curve downward due to the surface tension as shown in FIG. 7, there are certain ambiguous zones (errors) for the positions of the first and second hidden interfaces according to these curved portions. As the thickness of the second material 42 along the z-axis is supposed to be 15 mm the second hidden interface between the second and third materials 42 and 43 is especially ambiguous, ascribable to the surface tension and the nonuniform precipitation in the solidification process of wax.

In FIG. 8, the loop antennas 6 mm in diameter D (circumference length of the loop: $0.59\ \lambda$) are used both for the radiation antenna 31 and the detection antenna 32. The distance between the radiation antenna 31 and the detection antenna 32 is set to be 35 mm (denoted by '◇' symbol) and 60 mm (denoted by '□' symbol), and the distance between the detection antenna 32 and the container 34 is fixed to be 5 mm.

As shown in FIG. 8, the peak of the transmitted power curve can identify the position of wax as the second material 42. And, the position of the first hidden interface between the first and second materials 41 and 42, and the position of the second hidden interface between the second and third materials 42 and 43 can also be identified by comparing the transmitted power level with the reference power level.

In FIG. 8, the data processor 13 shown in FIG. 7 calculate a first reference power level for the first hidden interface between the first and second materials 41 and 42, when the first hidden interface is irradiated with electromagnetic waves, by pre-storing in the memory of the data processor 13 the reference transmitted power level detected when the container 34 is filled with only the first material (water) 41, and the reference transmitted power level detected when the container 34 is filled with only the second material (wax) 42. Similarly, the data processor 13 further calculate a second reference power level for the second hidden interface between the second and third materials 42 and 43, when the second hidden interface is irradiated with electromagnetic waves, by pre-storing in the memory of the data processor 13 the reference transmitted power level detected when the container 34 is filled with only the second material (wax) 42, and the reference transmitted power level detected when the container 34 is filled with only the third material (water) 43.

Or, as a preliminary test, calibration curves such as those shown in FIG. 8 are obtained so that a first specific transmitted power level when the first hidden interface between the first and second materials 41 and 42 is irradiated with electromagnetic waves and pre-stored as the first reference power level, and a second specific transmitted power level when the second hidden interface between the second and third materials 42 and 43 is irradiated with electromagnetic waves and pre-stored as the second reference power level in the memory of the data processor 13, and the positions of the first and second hidden interfaces can be identified based upon these values. In FIG. 8, by setting the first and second reference power levels to $-86$ dBm, the position of the first hidden interface between the first and second materials 41 and 42, and the position of the second hidden interface between the second and third materials 42 and 43 are identified in approximately 3 mm to 1 mm ($\cong \lambda/10$ to $\lambda/30$) resolution.

[When a Horn Antenna is Used as a Radiation Antenna]

FIG. 9 shows the results from irradiating a 9.4-GHz electromagnetic wave using a pyramidal horn antenna as the radiation antenna 31. In this case, a loop antenna 6 mm in diameter D is used as the detection antenna 32. The distance between the detection antenna 32 and the container 34 is set to 10 mm.

FIG. 9 shows the relationship between the transmitted power detected by the detection antenna 32 and the relative position of the probe (detection antenna) 32 with respect to the container 34 along the z-axis. Water, oil (lard oil) and water are used as the first, second and third materials 41, 42 and 43, respectively, and the first hidden interface between water and the oil, or the second hidden interface between the oil and water is irradiated with a 9.4-GHz electromagnetic wave.

The relative position of the detection antenna with respect to the container 34 shown in the abscissa is measured along the z-axis, and the origin (z=0 mm) is assigned to the position of the first hidden interface, and z=13 mm is assigned to the position of the second hidden interface. Similarly to the measurement condition by which the data shown in FIG. 8 is obtained, the data shown in FIG. 9 is obtained under the condition such that the positions of the detection antenna 32 and the radiation antenna 31 are fixed and the position of the container 34 is shifted along the z-axis. In this case, since the first hidden interface between the first and second materials 41 and 42, and the second hidden interface between the second and third materials 42 and 43 convexly curve downward due to the surface tension as shown in FIG. 7, there are certain ambiguous zones (errors) for the positions of the first and second hidden interfaces according to these curved portions.

As shown in FIG. 9, the peak of the transmitted power curve can identify the central position of the oil layer, which is employed as the second material 42. And, the position of the first hidden interface between the first and second materials 41 and 42, and the position of the second hidden interface between the second and third materials 42 and 43 can also be identified by comparing the transmitted power level with the reference power level.

In FIG. 9, the data processor 13 shown in FIG. 7 calculates a first reference power level for the first hidden interface between the first and second materials 41 and 42, when the first hidden interface is irradiated with electromagnetic waves, by pre-storing in the memory of the data processor 13 the reference transmitted power level detected when the container 34 is filled with only the first material (water) 41, and the reference transmitted power level detected when the container 34 is filled with only the second material (oil) 42. Similarly, the data processor 13 further calculate a second reference power level for the second hidden interface between the second and third materials 42 and 43, when the second hidden interface is irradiated with electromagnetic waves, by pre-storing in the memory of the data processor 13 the reference transmitted power level detected when the container 34 is filled with only the second material (oil) 42, and the reference transmitted power level detected when the container 34 is filled with only the third material (water) 43.

Or, as a preliminary test, calibration curves such as those shown in FIG. 9 is obtained so that a first specific transmitted power level when the first hidden interface between the first and second materials 41 and 42 is irradiated with electromagnetic waves and pre-stored as the first reference power level, and a second specific transmitted power level when the second hidden interface between the second and third materials 42 and 43 is irradiated with electromagnetic waves and pre-stored as the second reference power level in the memory of the data processor 13, and the positions of the first and second hidden interfaces can be identified based upon these values. In FIG. 9, by setting the first and second reference power levels to −80 to −86 dBm, the position of the first hidden interface between the first and second materials 41 and 42, and the position of the second hidden interface between the second and third materials 42 and 43 are identified.

FIG. 9 shows the relationships between the transmitted powers detected by three topologies of the detection antenna 32, in which the relative positions of the probe (detection antenna) 32 with respect to the container 34 are displaced along the line perpendicular to the plane of the paper, or the relative positions of the probe (detection antenna) 32 with respect to the container 34 are horizontally (along the x-axis) displaced so that main streams of the electromagnetic wave propagate through the left side (denoted by a '◇' symbol), the center (denoted by '□' symbol), and the right side (denoted by '△' symbol) of the container 34, respectively, when the direction along the radiation antenna 31 to the detection antenna 32 is defined as the y-axis. As shown in FIG. 9, three curves representing the relationships of the transmitted powers vs. the vertical probe positions along the z-axis, detected by three topologies of the detection antenna 32 along the x-axis, there are no significant differences between them.

As described above, according to the interface detection apparatus and method of the second embodiment of the present invention, the absolute positions of the first and second hidden interfaces of materials in an optically opaque environment may be detected externally without making contact with them.

Third Embodiment

In the interface detection apparatus of the first embodiment, the first anti-reflection plate 21 and the second anti-reflection plate 22 are facing in parallel so as to sandwich the container 34. By enclosing the container 34 with a cylindrical anti-reflection plate (or anti-reflection cylinder) 23, the measurement accuracy and sensitivity can be improved.

Figure 10:
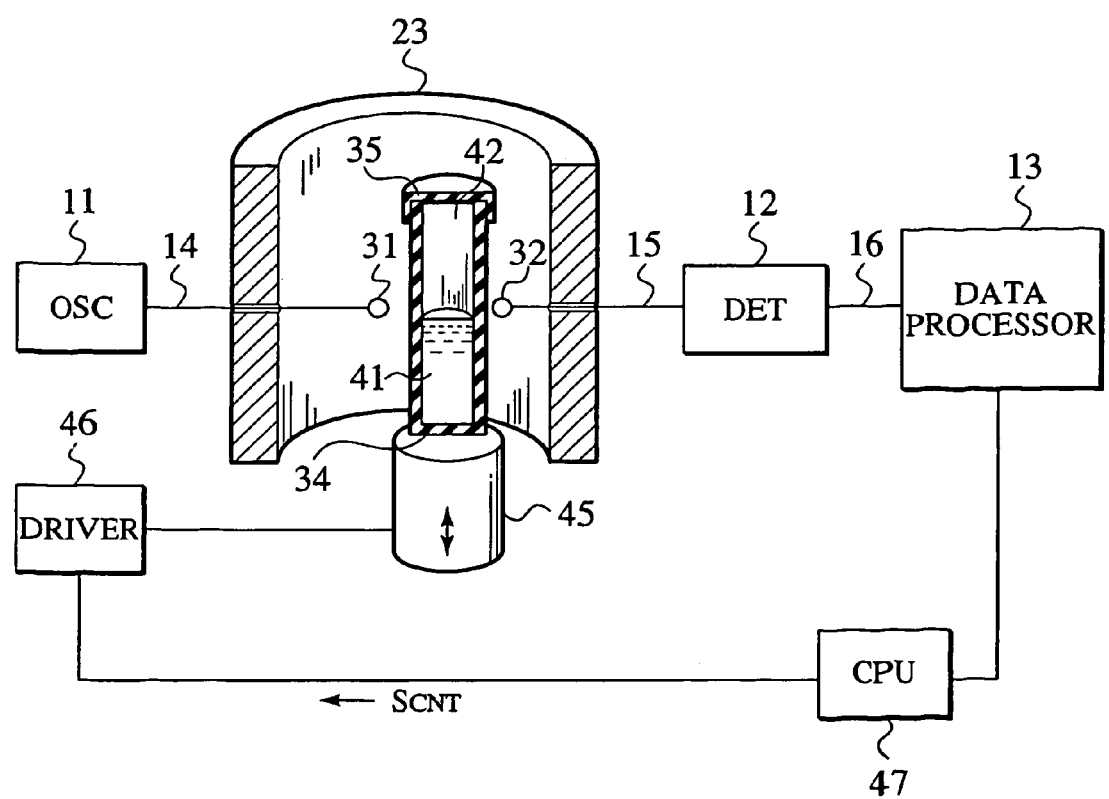
FIG. 10 is a schematic diagram for describing the configuration of an interface detection apparatus according to a third embodiment of the present invention.

As shown in FIG. 10, the interface detection apparatus according to the third embodiment of the present invention encompasses an irradiation mechanism (11, 14, 31), which irradiates electromagnetic waves onto a sample (34, 35, 41, 42) having the interface, a detection mechanism (32, 15, 12), which detects electromagnetic waves that have passed through the sample (34, 35, 41, 42), and a traveling mechanism (45, 46), which changes the relative position of the interface of the materials with respect to the detection mechanism (32, 15, 12). Similarly to the interface detection apparatus of the first embodiment, in the interface detection apparatus of the third embodiment, the irradiation mechanism (11, 14, 31) includes an oscillator 11, a transmitter side cable 14, which is connected to the oscillator 11, and a radiation antenna (transmitting antenna) 31, which is connected to the transmitter side cable 14. In addition, the detection mechanism (32, 15, 12) includes a detection antenna (receiving antenna) 32, a detector side cable 15, which is connected to the detection antenna 32, and a detector 12, which is connected to the detector side cable 15.

The interface detection apparatus according to the third embodiment shown in FIG. 10 further includes a cylindrical anti-reflection plate 23 configured to encircle around the outer cylindrical surface of the container 34. By using transparent electrode such as tin (Sn) doped indium oxide ($In_2O_3$) called 'ITO', indium (In) doped zinc oxide (ZnO) called 'IZO', gallium (Ga) doped zinc oxide (ZnO) called 'GZO', or tin oxide ($SnO_2$) for the substance of the cylindrical anti-reflection plate 23, the container 34 can be observed through the cylindrical anti-reflection plate 23, and the measurements of the interface detection become easier.

In the interface detection apparatus according to the third embodiment shown in FIG. 10, the oscillator 11 radiates electromagnetic waves to the outside via the transmitter side cable 14, the cylindrical anti-reflection plate 23, and the radiation antenna (loop antenna) 31. The radiated electromagnetic waves from the radiation antenna 31 propagate through the container 34 and the first or second materials 41 or 42 contained therein, and are then gathered by the detection antenna (loop antenna) 32. An output from the detection antenna 32 goes through the detector side cable 15 and then the cylindrical anti-reflection plate 23, and ends up being detected by the detector 12. The data processor 13 performs certain data processing for the detected signal.

To identify the absolute position of the hidden interface between the first and second materials 41 and 42, a methodology of moving the positions of both the radiation antenna 31 and the detection antenna 32 while fixing the position of the container 34, or a methodology of moving the position of the container 34 while fixing the positions of the radiation antenna 31 and the detection antenna 32 can be employed. The traveling mechanism (45, 46) shown in FIG. 10 encompasses a z-axis traveling stage 45 mounting the container 34, which has a linear guiding mechanism configured to shift the position of the container 34 along the z-axis, and a z-axis driver 46 configured to drive the movement of the z-axis traveling stage 45. In FIG. 10, an example in which the positions of the radiation antenna 31 and the detection antenna 32 are fixed and the position of the container 34 is shifted is shown. The z-axis driver 46 implemented by a step motor, a servomotor, or a linear motor, etc controls the position of the z-axis traveling stage 45, and a CPU 47, which is connected to the data processor 13, controls the operation of the z-axis traveling stage 45. The interface detection apparatuses of the first and second embodiments are different from the interface detection apparatus of the third embodiment, in that the CPU 47, outputs the control signal $S_{CNT}$ to the z-axis driver 46. However, an organization so that the data processor 13 outputs the control signal $S_{CNT}$ to the z-axis driver 46, similar to the interface detection apparatuses of the first and second embodiments can also be employed, of course. Anyhow, the z-axis driver 46 is controlled in conformity with the control signal $S_{CNT}$, so as to drive the z-axis traveling stage 45 shifting the relative position of the sample (34, 35, 41, 42) in a predetermined direction (along the z-axis) with respect to the cylindrical anti-reflection plate 23.

On the contrary, the position of the cylindrical anti-reflection plate 23 can be moved along the z-axis by the z-axis traveling stage 45 so that the positions of the radiation antenna 31 and the detection antenna 32 are fixed to the cylindrical anti-reflection plate 23 and can move simultaneously along the z-axis, while fixing the position of the container 34. In this case, a portion of the detector side cable 15 between the cylindrical anti-reflection plate 23 and the detector 12 is made of a flexible cable so that the position of the detection antenna 32 can travel freely along the z-axis while maintaining the position of the detector 12 at a fixed position, while the perpendicularly protruding end portions of the cables 14 and 15 from the inner surface plane of the cylindrical anti-reflection plate 23, disposed between the container 34 and the cylindrical anti-reflection plate 23, are made of rigid cables so that the vertical position of the tips of the radiation antenna 31 and the detection antenna 32 can be exactly determined by the vertical position of the cylindrical anti-reflection plate 23, by mounting the cylindrical anti-reflection plate 23 on the z-axis traveling stage 45 as shown in FIG. 10.

As described above, according to the interface detection apparatus and method of the third embodiment of the present invention, the position of the hidden interface of materials in an optically opaque environment may be detected externally without making contact with them with a higher accuracy than that achieved by the interface detection apparatus and method of the first embodiment. Other structures and materials are similar to the structure and materials already explained in the first and second embodiments, and overlapping or redundant descriptions may be omitted in the third embodiment.

OTHER EMBODIMENTS

Various modifications will become possible for those skilled in the art after receiving the teaching of the present disclosure without departing from the scope thereof.

Figure 11:
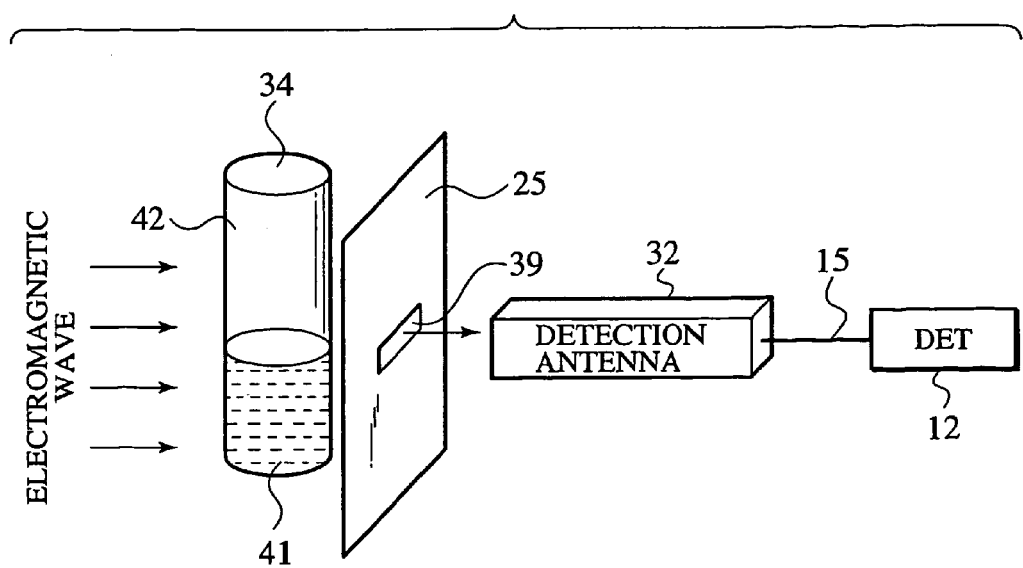
FIG. 11 is a schematic diagram for describing the configuration of an interface detection apparatus according to another embodiment of the present invention.
Figure 12:
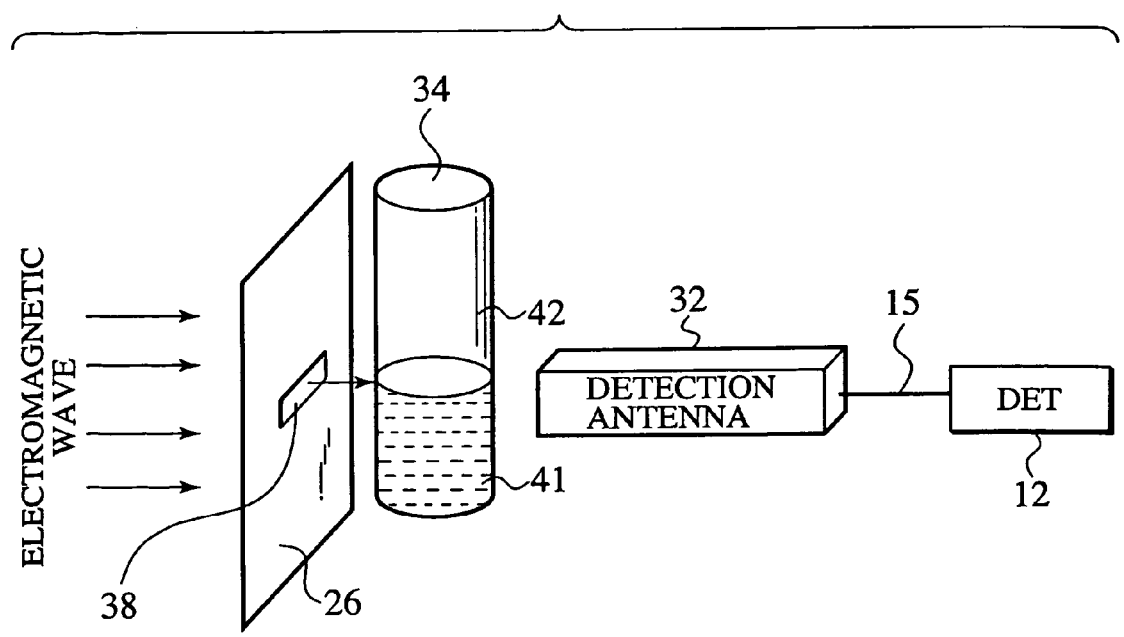
FIG. 12 is a schematic diagram for describing the configuration of an interface detection apparatus according to yet another embodiment of the present invention.

For example, as shown in FIGS. 11 and 12, a exit aperture plate 25 or an entrance aperture plate 26 may be inserted, which are provided respectively with a rectangular exit aperture 39 or a rectangular entrance aperture 38 in the electromagnetic wave propagation path so that only part of the electromagnetic wave can propagate through the rectangular exit aperture 39 or the rectangular entrance aperture 38, thereby improving accuracy of the measurement of the position of the hidden interface between the first and second materials 41 and 42.

In FIG. 11, an exit aperture plate 25 provided with a rectangular exit aperture 39 is inserted in the electromagnetic wave propagation path between the container 34 and detection antenna 32 so as to improve the accuracy of the measurement of the position of the hidden interface between the first and second materials 41 and 42. It is preferable to use a resonant aperture having a slit width of $\lambda/2$ for the rectangular exit aperture 39 so that the electromagnetic wave can radiate from the rectangular exit aperture 39 efficiently. The height of the rectangular exit aperture 39 should be as small as possible under the condition that required electromagnetic power can be radiated. By disposing of the exit aperture plate 25, the accuracy of the measurement of the position of the hidden interface between the first and second materials 41 and 42 can be improved. Aside from the loop antenna explained in the first to third embodiment, The loop antenna as shown in FIG. 1B is available for the radiation antenna 31 and the detection antenna 32. Furthermore, besides the loop antenna, various kinds of antennas such as a pyramidal horn antenna, a sectoral H-plane antenna, a sectoral E-plane antenna, a conical horn antenna, a paraboloid antenna, a dipole antenna, an array antenna, a patch antenna may be used as the radiation antenna 31 and the detection antenna 32.

In FIG. 12, an entrance aperture plate 26 provided with a rectangular entrance aperture 38 is inserted in the electromagnetic wave propagation path between a radiation antenna (illustration is omitted) and a container 34 so as to improve the accuracy of the measurement of the position of the hidden interface between the first and second materials 41 and 42. It is preferable to use a resonant aperture having a slit width of $\lambda/2$ for the rectangular entrance aperture 38 so that the electromagnetic wave can radiate from the rectangular entrance aperture 38 efficiently. The height of the rectangular entrance aperture 38 should be as small as possible under the condition that required electromagnetic power can be radiated.

Figure 13:
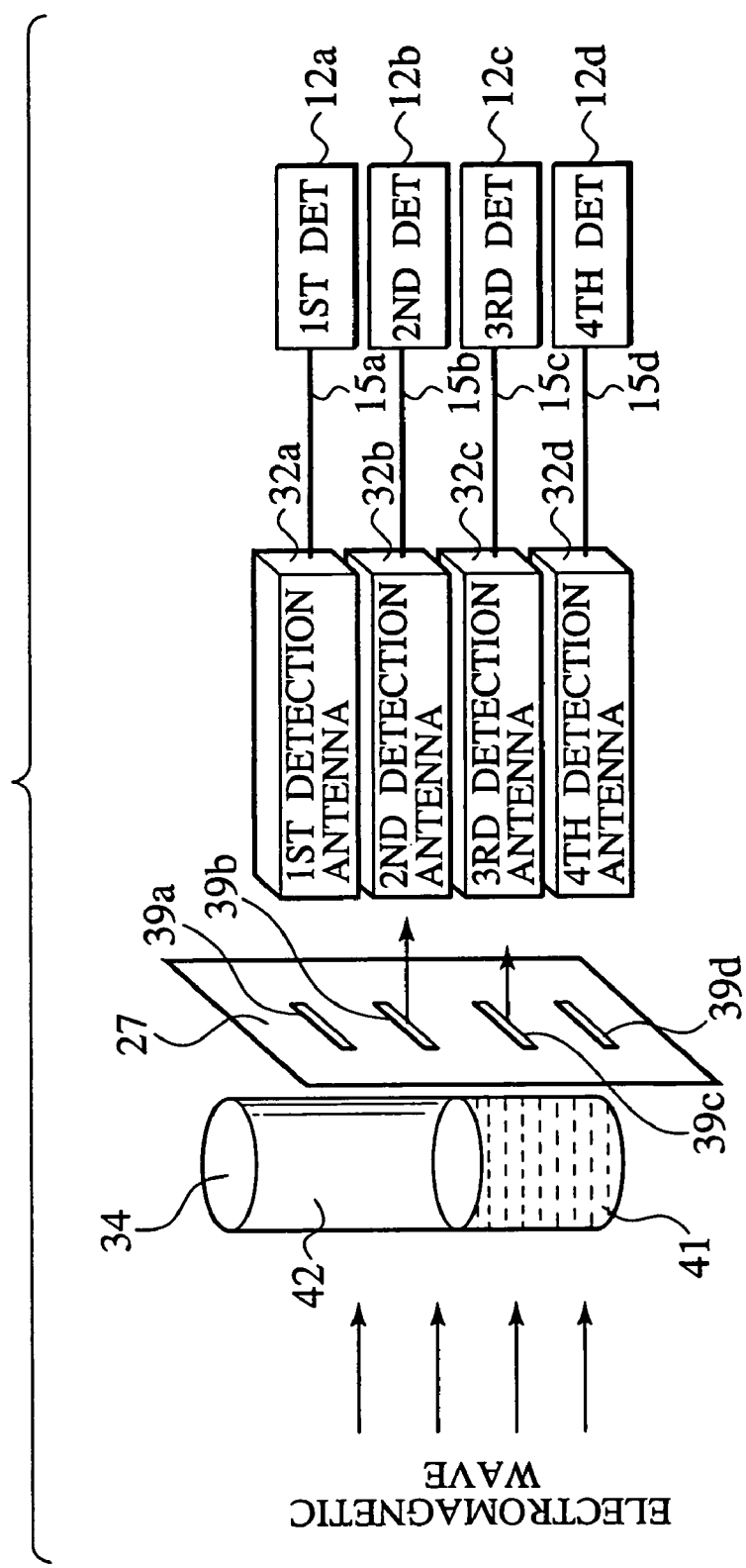
FIG. 13 is a schematic diagram for describing the configuration of an interface detection apparatus according to yet another embodiment of the present invention.

In FIG. 13, an exit aperture plate 27 provided with a plurality of exit apertures 39a, 39b, 39c, 39d is inserted in the electromagnetic wave propagation path between a container 34 and an array encompassing a first detection antenna 32a, a second detection antenna 32b, a third detection antenna 32c and a fourth detection antenna 32d. The first detection antenna 32a, the second detection antenna 32b, the third detection antenna 32c and the fourth detection antenna 32d are connected to a first detector 12a, a second detector 12b, a third detector 12c and a fourth detector 12, through a first detector side cable 15a, a second detector side cable 15b, a third detector side cable 15c and a fourth detector side cable 15d, respectively. As shown in FIG. 13, by detecting electromagnetic waves propagated through the first exit aperture 39a, the second exit aperture 39b, the third exit aperture 39c and the fourth exit aperture 39d with the first detector 12a, the second detector 12b, the third detector 12c and the fourth detector 12, respectively, the position of the hidden interface between the first and second materials 41 and 42 can be measured without employing the traveling mechanism (45, 46) as shown in FIG. 10. Various kinds of antennas such as loop antennas, pyramidal horn antennas, sectoral H-plane antennas, sectoral E-plane antennas, conical horn antennas, paraboloid antennas, dipole antennas, array antennas, patch antennas may be used as the first to fourth detection antennas 32a to 32d.

The flat aperture plates 25, 26 and 27 shown in FIGS. 11 to 13 can be made of the same substances as that of the anti-reflection plates 21 and 22 explained in the first embodiment. The configuration in which the flat entrance aperture plate 26 is deployed on the irradiation mechanism (11, 14, 31) side and the single exit aperture plate 25 has an exit aperture 39, or the multi-exit aperture plate 27 has an array of exit apertures 39a, 39b, 39c, 39d is deployed on the detection mechanism side, can also be employed. The distance between the container 34 and the exit aperture plate 25, 26 or 27 can be set to approximately zero, or the distance may be set to be several µm to several 100 µm.

Figure 14A:
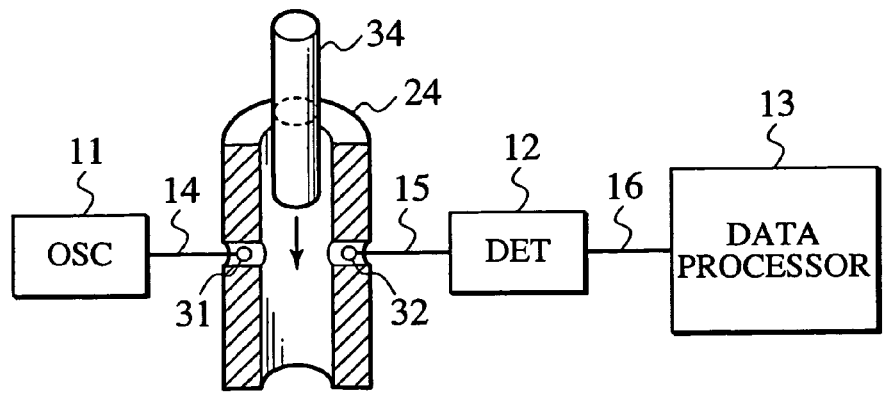
FIGS. 14A to 14C are schematic diagrams for describing the operation and configuration of an interface detection apparatus according to yet another embodiment of the present invention.
Figure 14B:
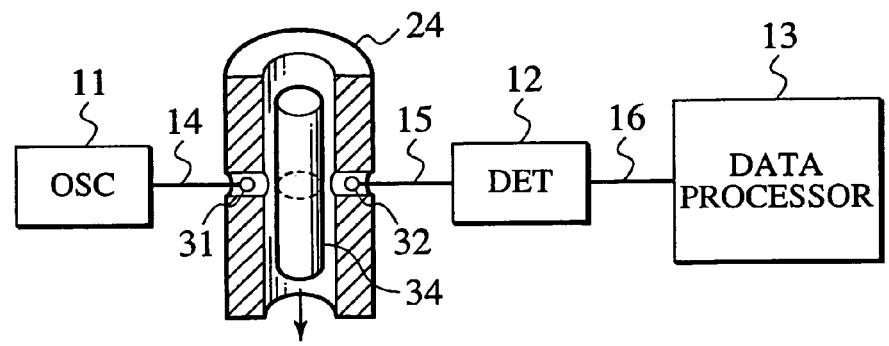
Figure 14C:
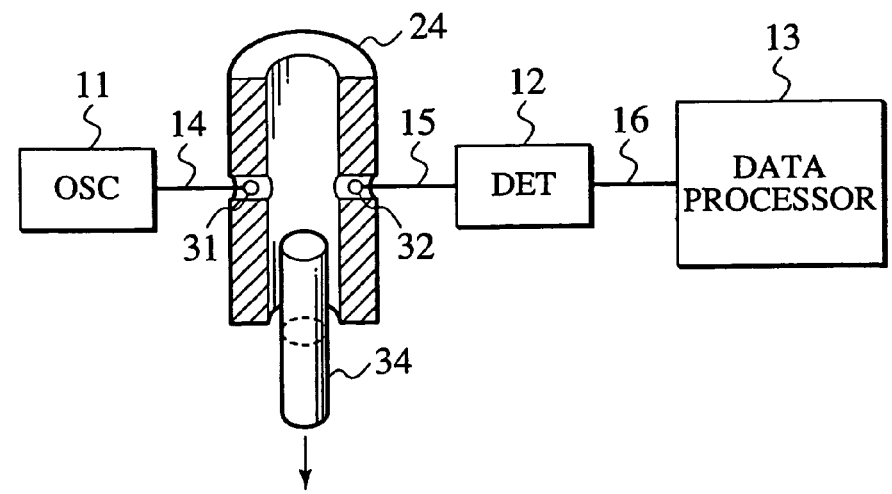

For example, as shown in FIGS. 14A, 14B and 14C, a cylindrical container 34 can be configured to path through the inner wall of a cylindrical aperture plate (aperture cylinder) 24 having an entrance aperture and an exit aperture in the wall, the inner diameter of the cylindrical aperture plate (aperture cylinder) 24 is slightly larger than the outer diameter of the container 34 so that the cylindrical container 34 can drop freely with gravity through air friction, promoted by air disposed in the gap between the outer diameter of the cylindrical container 34 and the inner wall of the cylindrical aperture plate 24. In other words, the traveling mechanism (45, 46) shown in FIG. 10 is implemented by air friction achieved in the cylindrical aperture plate 24 and the force of gravity, and the position of the container 34 can travel along the z-axis. Through the traveling mechanism shown in FIGS. 14A, 14B and 14C, the relative relation of the hidden interface between the first and second materials 41 and 42 vs. the detection mechanism (32, 15, 12) can be changed without using the z-axis driver 46 and the z-axis traveling stage 45 as shown in FIG. 10.

In the configuration so that the distance between the container 34 and the exit aperture plate 25, 26 or 27 is set to approximately zero, or in the configuration such as the cylindrical container 34 can pass through the inner wall of the cylindrical aperture plate 24, the inner diameter of the cylindrical aperture plate 24 is slightly larger than the outer diameter of the container 34, so at least part of the loop antennas 31 and/or 32 can be inserted in the entrance aperture and/or the exit aperture provided in the wall of the cylindrical aperture plate 24 as shown in FIGS. 14A, 14B and 14C.

Because liquid is contained in the container 34, the cases in which a plurality of materials are stacked along the z-axis, or the direction of gravity, and the positions of the radiation antenna 31 and the detection antenna 32 are moved along the z-axis while the position of the container 34 is fixed, or the position of the container 34 is moved along the z-axis while the position of the radiation antenna 31 and the detection antenna 32 are fixed are explained in the first to third embodiments, referring to FIGS. 2 to 6, 8 and 9. However, the stacking direction of the materials in the container 34 is not limited to the z-axis. For example, in the case of the identification of the absolute position of the hidden interface in the composite substances made of a plurality of solid materials such as plywood, multi-layered timber or multi-layered mortar, the direction along which the position of the hidden interface is detected can be selected along a horizontal direction. Furthermore, in the case of the identification of the absolute position of the hidden interface in the plywood, or mortar, the container 34 can be omitted.

The identification of the absolute position of the hidden interface is not limited to a linear measurement, or one-dimensional measurement, but an area measurement scanning over a two-dimensional plane can be employed, using a two-dimensional antenna array. For example, a hidden crack formed in a mortal wall can be detected by scanning two-dimensionally with a radiation of sub millimeter wave or terahertz waves. The detection of the hidden crack in the mortal wall corresponds to a case that mortal, air, and mortal are assigned respectively as the first, second and third materials 41, 42 and 43, in the second embodiment. The area scanning of the radiation of sub-millimeter wave or terahertz waves can detect the inner hidden crack deeply lying in the mortal wall.

In the interface detection according to the second embodiment, the sample (34, 35, 41, 42, 43) implemented by the first material 41, the second material 42 and the third material 43 are contained in the container 34 so as to form a triple layered structure is explained, but it will be understood for a person skilled in the art that the technical features and subject matter of the present invention can be applicable to the identification of the absolute position of the hidden interface in a multi-layered structure, which is implemented by a plurality of material layers more than a quadruple of layers in light of the disclosure mentioned above.

In the interface detection apparatus of the first embodiment shown in FIG. 1A and that of the second embodiment shown in FIG. 7, a first anti-reflection plate 21 is deployed on the irradiation mechanism (11, 14, 31) side, and a second anti-reflection plate 22 is deployed on the detection mechanism (32, 15, 12) side; wherein the flat anti-reflection plates 21 and 22 face each other and sandwich the container 34. However, if we monolithically integrate Gunn diodes, IMPATT diodes, TUNNETT diodes, HEMTs, HBTs, or SITs in a minute semiconductor chip so as to implement the oscillator 11, the oscillator 11 can be mounted on the outer surface of the flat anti-reflection plates 21, or on the inner surface of the flat anti-reflection plates 21 facing the container 34. Similarly, if we use a small sized Schottky diode or bolometer, or if we monolithically integrate Schottky diode, or bolometer with a low noise amplifier in a minute semiconductor chip so as to implement the detector 12, the detector 12 can be mounted on the outer surface of the flat anti-reflection plates 22, or on the inner surface of the flat anti-reflection plate 22 facing the container 34. These architectures can also be applied to the interface detection apparatus of the third embodiment shown in FIG. 10, by mounting the oscillator 11 and/or the detector 12 on the outer surface of the cylindrical anti-reflection plate 23, or on the inner surface of the cylindrical anti-reflection plate 23 facing the container 34. Furthermore, the detector side cable 15 connected to the detection antenna 32 can be omitted, if the detector 12 is mounted on the inner surface of the flat anti-reflection plate 22 or the cylindrical anti-reflection plate 23, by using a whisker antenna directly protruding from the Schottky electrode of the submillimeter detecting Schottky diode as the detection antenna 32.

In the first to third embodiments, methodologies using a single frequency for detecting the position of the interface were disclosed, but the identification of the absolute position of the hidden interface can be achieved by a measurement using multi frequencies. In this case, an array of oscillators may be prepared for providing the multi frequencies, although it is possible to transmit the multi frequencies from a single oscillator 11. By assembling a measurement system encompassing mainly a network analyzer and the detector 12, the detection frequency may be swept so as to achieve the measurement of the position of the interface, using substantially the same principles disclosed in the first to third embodiments. By sweeping the detection frequency so as to irradiate on the first material 41 and/or the second material 42 (or further the third material 43), a relationship between the relative position of the probe and the corresponding transmitted power, the relation is ascribable to complex dielectric constant (dielectric relaxation spectrum) of the first material 41 and/or the second material 42 (or further the third material 43), can be obtained. By analyzing the relation in the data processor 13, a more highly precise measurement can be achieved.

The electromagnetic wave configured to irradiate the first material 41 and/or the second material 42 (or further the third material 43) is not required to be a continuous sine wave. For example, by applying a step pulse to the first material 41 and/or the second material 42 (or further the third material 43), and then by Fourier transforming the data of the time domain, which were detected by the detector 12, in the data processor 13, the position of the interface can be measured.

For a specific size of the first material 41, the second material 42 or the third material 43, and the frequency of the electromagnetic wave to be employed, there may be a situation in that the temperature of the first material 41, the second material 42 or the third material 43 rises. In view of these situations, a cooling device may be established in the container 34 such as in the configurations shown in FIGS. 1A, 7 and 10.

Thus, the present invention of course includes various embodiments and modifications and of the like which are not detailed above. Therefore, the scope of the present invention will be defined in the following claims.

The interface detection apparatus and method of the first to third embodiments of the present invention can be used in medical equipment and the food test field to measure samples contained in containers 34 with labels or the like attached thereon concealing the interior. The interface detection apparatus and method of the first to third embodiments can be also used to examine an internal configuration in the civil engineering and architecture fields. Furthermore, the interface detection apparatus and method of the first to third embodiments can be used for chemical plants to measure the liquid level of corrosive chemical into which a sensor cannot be introduced. Moreover, the interface detection apparatus and method of the first to third embodiments can be used to inspect parts of aircrafts and vehicles, which allow electromagnetic waves to pass through.

This application claims benefit of priority under 35 USC 119 based on Japanese Patent Application No. P2004-01147 filed Jan. 19, 2004, the entire contents of which are incorporated by reference herein.

What is claimed is:

1. An interface detection apparatus for detecting the position of a hidden interface between first and second materials, the first material having a different physical property from the second material, comprising:
   an irradiation mechanism configured to irradiate an electromagnetic wave onto a sample wherein the sample comprises the first and second materials, and wherein the irradiation mechanism comprises:
      an oscillator configured to generate the electromagnetic wave; and
      a radiation antenna electrically connected to the oscillator, configured to radiate the electromagnetic wave onto the sample;
   a detection mechanism configured to detect the electromagnetic wave that has passed through the sample;
   a traveling mechanism configured to change the relative position of the hidden interface with respect to the position of the detection mechanism; and
   an entrance aperture plate disposed between the radiation antenna and the oscillator, wherein the entrance aperture plate is provided with an entrance aperture configured to pass through a part of the electromagnetic wave.

2. The interface detection apparatus of claim 1, wherein the distance between the irradiation mechanism and the detection mechanism is less than 15 times the wavelength of the electromagnetic wave.

3. The interface detection apparatus of claim 1, wherein the detection mechanism comprises:
   a detection antenna configured to receive the electromagnetic wave; and
   a detector electrically connected to the detection antenna, configured to detect information relating to the interface carried by the electromagnetic wave.

4. The interface detection apparatus of claim 3, further comprising an exit aperture plate disposed between the sample and the detection antenna, the exit aperture plate is provided with an exit aperture configured to pass through a part of the electromagnetic wave.

5. The interface detection apparatus of claim 3, further comprising an exit aperture plate disposed between the sample and the detection antenna, the exit aperture plate is provided with a plurality of exit apertures, each of the exit apertures are configured to pass through a part of the electromagnetic wave.

6. The interface detection apparatus of claim 3, further comprising a detector side cable connecting the detection antenna to the detector.

7. The interface detection apparatus of claim 6, further comprising an anti-reflection plate disposed between the detection antenna and the detector, having an aperture for passing through the detector side cable.

8. The interface detection apparatus of claim 6, wherein the entrance aperture plate comprises a cylindrical anti-reflection plate enclosing the sample, having the entrance aperture for penetrating a transmitter side cable so as to connect the oscillator to the radiation antenna, and an exit aperture for penetrating a detector side cable so as to connect the detection antenna to the detector.

9. The interface detection apparatus of claim 1, wherein the radiation antenna comprises a horn antenna or a loop antenna.

10. The interface detection apparatus of claim 3, wherein the detection antenna comprises a loop antenna.

11. The interface detection apparatus of claim 10, wherein the circumference length of the loop antenna is smaller than the wavelength of the electromagnetic wave.

12. The interface detection apparatus of claim 1, further comprising a transmitter side cable connecting the radiation antenna to the oscillator.

13. The interface detection apparatus of claim 1, further comprising a data processor electrically connected to the detector, configured to accept output signals from the detector, to execute a process along with a program based upon the accepted data to define an absolute position of the hidden interface with respect to a reference position.

14. The interface detection apparatus of claim 13, wherein the data processor records a relationship between transmitted powers of the electromagnetic wave and relative positions of the detection mechanism.

15. An interface detection method for detecting a position of a hidden interface between first and second materials, the first material having a different physical property from the second material, comprising:

irradiating an electromagnetic wave onto a sample, through an entrance aperture plate disposed between a radiation antenna and an oscillator configured to irradiate the electromagnetic wave so that a part of the electromagnetic wave can pass through the entrance aperture plate, wherein the sample comprises the first and second materials;

detecting the electromagnetic wave that has passed through the sample by a detection mechanism;

changing relative positions of the hidden interface with respect to a position of the detection mechanism; and determining an absolute position of the hidden interface with respect to a reference position.

16. The interface detection method of claim 15, further comprising:

obtaining a specific transmitted power level as a reference power level or a specific phase of transmitted electromagnetic wave as a reference phase by using a reference sample, after irradiating with the electromagnetic wave on to a known interface of the reference sample; and storing the reference power level or the reference phase in a memory of a data processor, wherein the absolute position of the hidden interface is determined by comparing the measured transmitted power level with the reference power level, or by comparing the measured phase of transmitted power level with the reference phase.

* * * * *